United States Patent

Ouchi

[11] Patent Number: 6,117,141
[45] Date of Patent: Sep. 12, 2000

[54] ENDOSCOPIC DRAINAGE TUBE HOLDER

[75] Inventor: Teruo Ouchi, Saitama, Japan

[73] Assignee: Asahi Kogaku Kogyo Kabushiki Kaisha, Tokyo, Japan

[21] Appl. No.: 09/222,888

[22] Filed: Dec. 30, 1998

[30] Foreign Application Priority Data

| Jan. 5, 1998 | [JP] | Japan | 10-000021 |
| Mar. 19, 1998 | [JP] | Japan | 10-069592 |
| Aug. 4, 1998 | [JP] | Japan | 10-220123 |

[51] Int. Cl.[7] ............................ A61F 11/00
[52] U.S. Cl. ............... 606/108; 606/194; 606/192
[58] Field of Search ................ 606/108, 191, 606/192, 194, 195, 198; 623/1, 3; 128/898; 604/104, 96, 97, 98, 99

[56] References Cited

U.S. PATENT DOCUMENTS

| 4,981,482 | 1/1991 | Ichikawa | 606/108 |
| 5,601,533 | 2/1997 | Hancke et al. | |
| 5,769,868 | 6/1998 | Yock | 606/194 |
| 5,823,995 | 10/1998 | Fitzmaurice et al. | 604/96 |
| 5,876,375 | 3/1999 | Penny | 604/96 |
| 5,910,145 | 6/1999 | Fischell et al. | 606/108 |
| 5,976,153 | 11/1999 | Fischell et al. | 606/108 |
| 5,984,945 | 11/1999 | Sirhan | 606/194 |

FOREIGN PATENT DOCUMENTS

| 57-99941 | 6/1982 | Japan . |
| 63-7205 | 3/1988 | Japan . |
| 63-24883 | 7/1988 | Japan . |
| 9-103433 | 4/1997 | Japan . |
| 9-306710 | 11/1997 | Japan . |

*Primary Examiner*—Gene Mancene
*Assistant Examiner*—Pedro Philogene
*Attorney, Agent, or Firm*—Greenblum & Bernstein, P.L.C.

[57] ABSTRACT

An endoscopic drainage tube holder, to be inserted into a treating tool insertion channel of an endoscope, including an insertion guide and a fixing unit. The insertion guide is provided on an outside of an inlet of the treating tool insertion channel so as to guide at least one of a side end portion of a pusher and a side end portion of a guide wire. The fixing unit fixes at least one of the side end portion of the pusher and the side end portion of the guide wire, which are guided by the insertion guide, to the insertion guide.

16 Claims, 26 Drawing Sheets

FIG. 32
FIG. 33
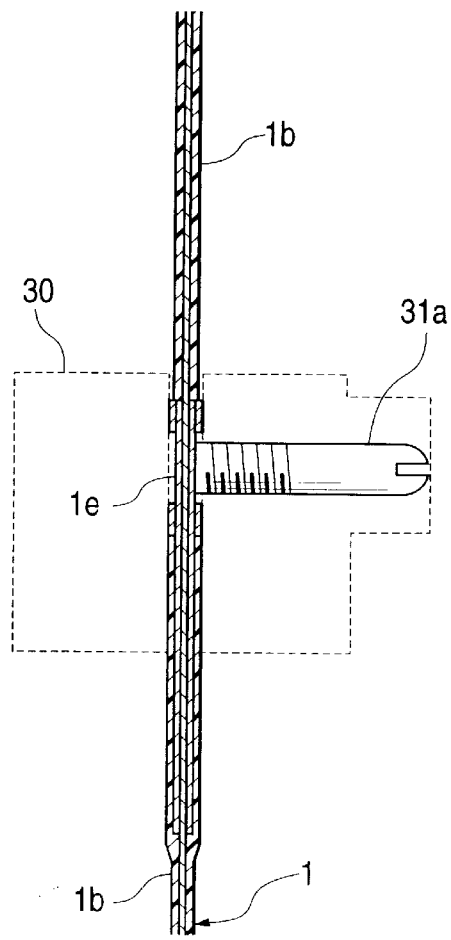
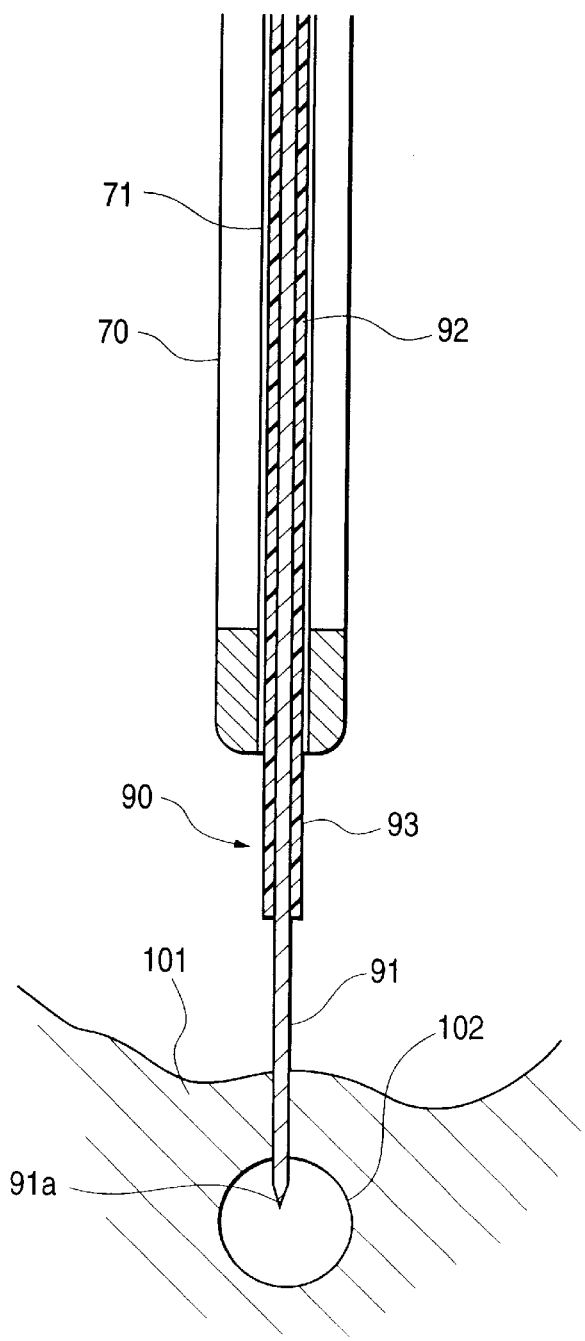

ENDOSCOPIC DRAINAGE TUBE HOLDER

BACKGROUND OF THE INVENTION

1. Field of the Invention

The present invention relates to an endoscopic drainage tube holder that is inserted into an endoscope treating tool insertion channel to hold a drainage tube in a body cavity.

2. Description of the Related Art

In order to exhaust secreting fluid stored in the pancreatic duct, the biliary duct, etc., there is an operation for holding a drainage tube in the human body via an endoscope. In the related art, first the pancreatic duct, the biliary duct, etc. are pricked by a pricker, through which a guide wire is attachably/detachably inserted, from the wall of the body cavity via a treating tool insertion channel of the endoscope (particularly, an ultrasonic endoscope).

Then, the drainage tube is inserted into a hole, which is formed by piercing using the guide wire as a guide, while leaving the top end of the guide wire in the diseased part. Finally, the guide wire is pulled out such that the drainage tube is left in the pancreatic duct and the stomach, or left to spread over the pancreatic duct and the duodenum.

The related endoscopic pricker used in such an operation is constructed so that the inner tube, to the top end of which a tubular needle (e.g., an injection needle) is provided and to which the guide wire is detachably attached, is inserted into an outer sleeve. The outer sleeve can be inserted/extracted into/from the treating tool insertion channel of the endoscope along the axial direction thereof.

In order to hold the drainage tube using the endoscope, as described above, troublesome operations are required. That is, after the pricker has pierced the pancreatic duct, the pricker is pulled out while leaving the top end of the guide wire in the pancreatic duct, and then the drainage tube is inserted into the pancreatic duct using the guide wire as a guide. In particular, it is very difficult and troublesome to remove only the pricker, while preventing the top end of the guide wire from being pulled out from the pancreatic duct or the biliary duct.

Therefore, a patent application, disclosing an endoscopic drainage tube holder in which, after the pricker has pierced the tissue in the body cavity via the endoscope, the drainage tube can be held easily in such pricker, has been previously filed by the inventors of the present invention (Patent Application No. Hei 9-306710).

The gist of the configuration of the previous endoscope drainage tube holder is that the pricker for pricking the organic tissue is provided at the top end of the flexible guide wire that guides the drainage tube. Then, the drainage tube is fitted on the guide wire at a position in the vicinity of the top end, and held there by frictional resistance. The pusher, which is formed of the flexible tube to push the drainage tube in the forward direction, is then fitted loosely on the guide wire.

FIG. 33 shows a situation in which such a drainage tube holder 90 is passed through a treating tool insertion channel 71 of an ultrasonic endoscope 70. The pricker 91a formed on the top end of the guide wire 91 then pricks into the pancreatic duct 102 from the stomach wall 101. Under this condition, the drainage tube 93 may next be inserted by pushing the pusher 92, which is fitted loosely onto the guide wire 91, until the top end of the drainage tube 93 reaches the pancreatic duct 102.

However, in this configuration in which the guide wire 91 and the pusher 92 can be independently pushed forward in the side operating portion (not shown) for executing the pushing operation, it is very difficult not to move the guide wire 91 when the pusher 92 is pushed in the forward direction. If the guide wire 91 is moved, the pricker 91a formed on the top end may be extracted from the pancreatic duct 102, or conversely the pricker 91a may break through the pancreatic duct 102.

In addition, if both hands must be used to push only the pusher 92 forward, while simultaneously pressing the guide wire 91 so that the guide wire 91 does not move with the pusher 92, an assistant is needed to operate the endoscopic drainage tube holder 90. Therefore, not only does it take much time and labor to operate the endoscopic drainage tube holder 90, it is very difficult for the operator to execute the operation precisely.

Besides, when the guide wire 91 is pulled from the inside after the drainage tube 93 has been set at the correct position, the drainage tube 93 as well as the guide wire 91 may be pulled out, and the drainage exhaustion is not performed. Sometimes the above operations must be repeated completely from the beginning of the operation.

SUMMARY OF THE INVENTION

It is an object of the present invention to provide an endoscopic drainage tube holder that overcomes the above-described problems.

More specifically, it is an object of the present invention to provide an endoscopic drainage tube holder that is capable of easily holding a drainage tube by virtue of only a pushing operation of a pusher executed by a single endoscope operator when a top end of a guide wire reaches a target region. Further, the holder can hold the drainage tube without disturbance of a set state of the drainage tube during extraction of the guide wire, after the drainage tube has been set correctly.

In order to achieve the above object, an endoscopic drainage tube holder, for insertion into a treating tool insertion channel of an endoscope, includes a flexible linear guiding wire, a drainage tube, a pusher, an insertion guide, and a fixing unit. The flexible linear guiding member has provided, at a top end thereof, a pricker for pricking into an organic tissue. The drainage tube is fitted on the linear guiding member near its top end position, and held there by frictional resistance. The pusher is formed of a flexible tube, which is loosely fitted onto the linear guiding member, such that the drainage tube can be pushed forward.

The insertion guide is provided on an outside of an inlet of the treating tool insertion channel, so as to guide at least one of a base end of the pusher and a base end of the linear guiding member.

The fixing unit fixes at least one of the base end of the pusher and the base end of the linear guiding member, which are guided by the insertion guide.

The fixing unit may fix the base end of the pusher to the insertion guide independently from the base end of the linear guiding member when the drainage tube is protruded from an outlet of the treating tool insertion channel. Alternatively, the fixing unit may fix the base end of the linear guiding member to the insertion guide independently from the base end of the pusher when the drainage tube is protruded from an outlet of the treating tool insertion channel.

Then, the base end of the linear guiding member may be coupled/released to/from the base end of the pusher. The pusher and the linear guiding member may be separated from each other, and the pusher and the linear guiding member may be separated from the insertion guide.

Also, the fixing unit maybe formed of a manual fastening screw, and the linear guiding member or the linear guiding member and the pusher may be released from the insertion guide by loosening the fastening screw.

A top end side of the insertion guide may be formed like an L-shaped projection that is bent shortly in a lateral direction. A through hole is formed in the L-shaped projection, and the fastening screw may be passed therethrough so as to close the through hole.

Further, the linear guiding member may be formed of a conductive guide wire, the pricker at the top end may be formed of a high frequency electrode, and a base end side of the guide wire may be connected attachably/detachably to a connection terminal to be connected to a high frequency power supply.

The flexible tube constituting the pusher may be electrically insulative. All or a part of the guide wire may be coated with an electrically insulating material.

Also, the linear guiding member may be formed of a flexible tube, and the pricker may be formed like a needle. The insertion guide may have flexibility.

In addition, the base end of the linear guiding member may be fixed/released at any location to/from the base end portion of the pusher.

The present invention relates to the subject matter contained in Japanese Patent applications Nos. Hei. 10-000021 filed on Jan. 5, 1998, Hei. 10-069592 filed on Mar. 19, 1998, and Hei. 10-220123 filed on Aug. 4, 1998, which are expressly incorporated herein by reference in their entireties.

BRIEF DESCRIPTION OF THE DRAWINGS

FIG. 32 is a fragmental sectional view showing a modification of the endoscopic drainage tube holder according to the seventh embodiment of the present invention; and FIG. 33 is a side sectional view showing a top end portion of an endoscopic drainage tube holder in the related art.

DETAILED DESCRIPTION OF AN ENDOSCOPIC DRAINAGE TUBE HOLDER

Explanations of the present invention will now be described in detail with reference to the accompanying drawings hereinafter.

Figure 1:
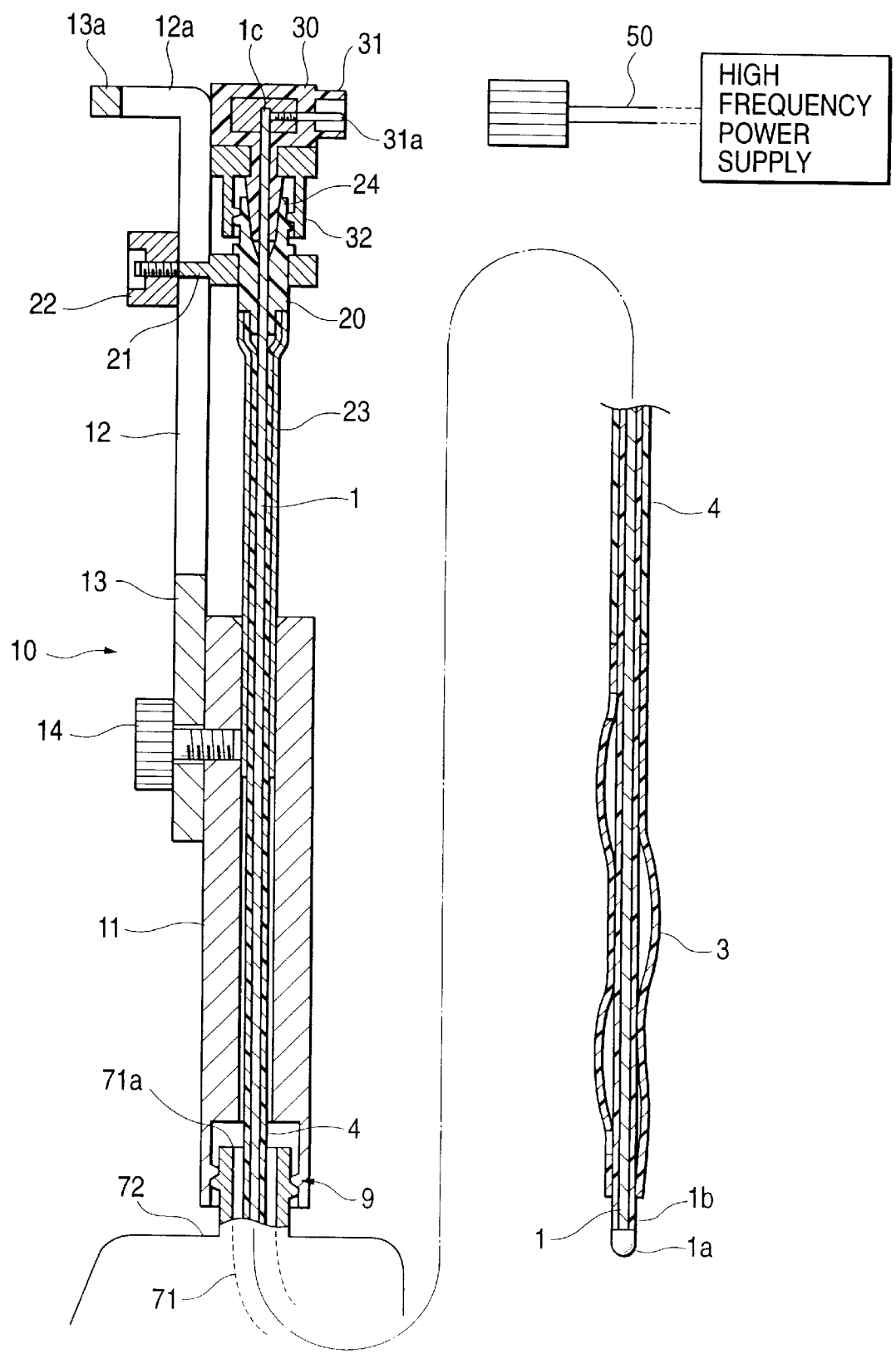
FIG. 1 is a side sectional view showing an endoscopic drainage tube holder according to a first embodiment of the present invention.

FIG. 1 shows an endoscopic drainage tube holder according to a first embodiment of the present invention. Reference 1 denotes a flexible guide wire (linear guiding member) made of a single or stranded wire of, for example, a conductive stainless steel wire. The total length of the guide wire 1 is formed to be longer than an endoscope treating tool insertion channel, by about 10 to 20 cm, for example.

A pricker 1a used to prick the organic tissue is formed at a top end portion of the guide wire 1. In the endoscopic drainage tube holder according to the first embodiment, a conductive high frequency electrode chip is formed as the pricker 1a, so that the high frequency current can be supplied to the pricker 1a from the side via the guide wire 1.

Then, an electrical insulating jacket 1b, which is formed of a tube or coating of ethylene tetrafluoride resin, polyimide resin, polyethylene resin, or the like, is coated on a either a part or all of the guide wire 1, but not on the pricker 1a. In the first endoscopic drainage tube holder, the insulating jacket 1b is provided on a top half portion of the guide wire 1, but such an insulating jacket 1b may be completely omitted.

While a top end of the high frequency electrode chip of the pricker 1a is formed in a hemispherical shell shape, various other shapes may be employed, such as an obliquely cut-out needle, a circular cone needle, a circular cone with a rounded top end, etc. The guide wire 1 that can mechanically prick using a sharp needle point without a supply of high frequency current may be employed.

A drainage tube 3, which is held to discharge the drainage from the body, covers the guide wire 1 at a position near the top end of the guide wire, a distance of about several mm to 1 cm from the pricker 1a, for example.

Figure 2:
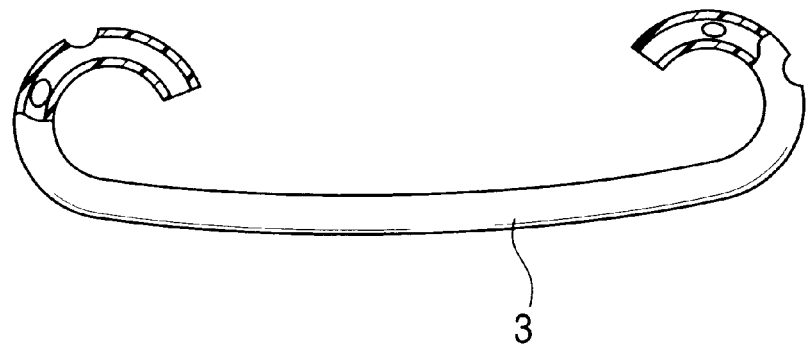
FIG. 2 is a side view showing a partially cut out pigtail type drainage tube.
Figure 3:
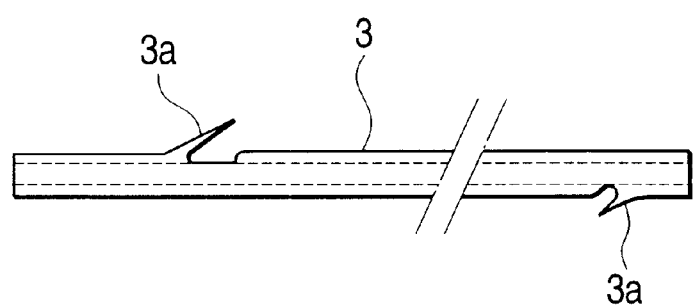
FIG. 3 is a side view showing a straight drainage tube.
Figure 4:
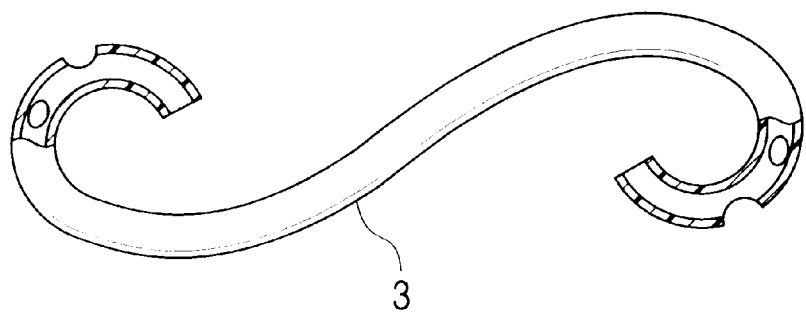
FIG. 4 is a partially cut out side view showing an S-shaped drainage tube.

As shown in FIG. 2, for example, this drainage tube 3 is a so-called pigtail type drainage tube whose both ends are curled in a free state. When the drainage tube 3 is held in the internal organs, the curled portions on both ends are placed in the internal organs to perform a role of an anchor. However, various other drainage tubes, such as a straight drainage tube 3 with prickles 3a shown in FIG. 3, an S-shaped drainage tube 3 shown in FIG. 4, etc., may be employed.

The pigtail type drainage tube 3 is formed of, for example, a non-rigid plastic such as fluorocarbon polymers. Such a drainage tube 3 straightens due to elastic deformation when fitted on the guide wire 1. The drainage tube 3 is then held on the guide wire 1 by a frictional resistance generated between the guide wire 1 and the drainage tube 3 by elasticity of the drainage tube 3 for returning to its original shape.

An outer shape of the top end side of the drainage tube 3 is formed in a smooth tapered shape, such that the drainage tube 3 can be pushed smoothly into a hole being formed in the organic tissue by the pricking.

In the side portion closer to the area where the drainage tube 3 is held, a pusher 4 that is formed of a flexible tube to push the drainage tube 3 in a forward direction is loosely fitted over the full length of the guide wire 1.

The pusher 4 is formed of an electrical insulating flexible tube made of ethylene tetrafluoride resin, polyimide resin, polyethylene resin, or the like. The pusher 4 is fitted to be moved back and forth with respect to the guide wire 1, such that a top end surface of the pusher 4 can contact a rear end surface of the drainage tube 3.

Accordingly, if the pusher 4 is pushed in a forward direction along the guide wire 1, the drainage tube 3 can be pushed out from the top end of the guide wire 1.

Figure 6:
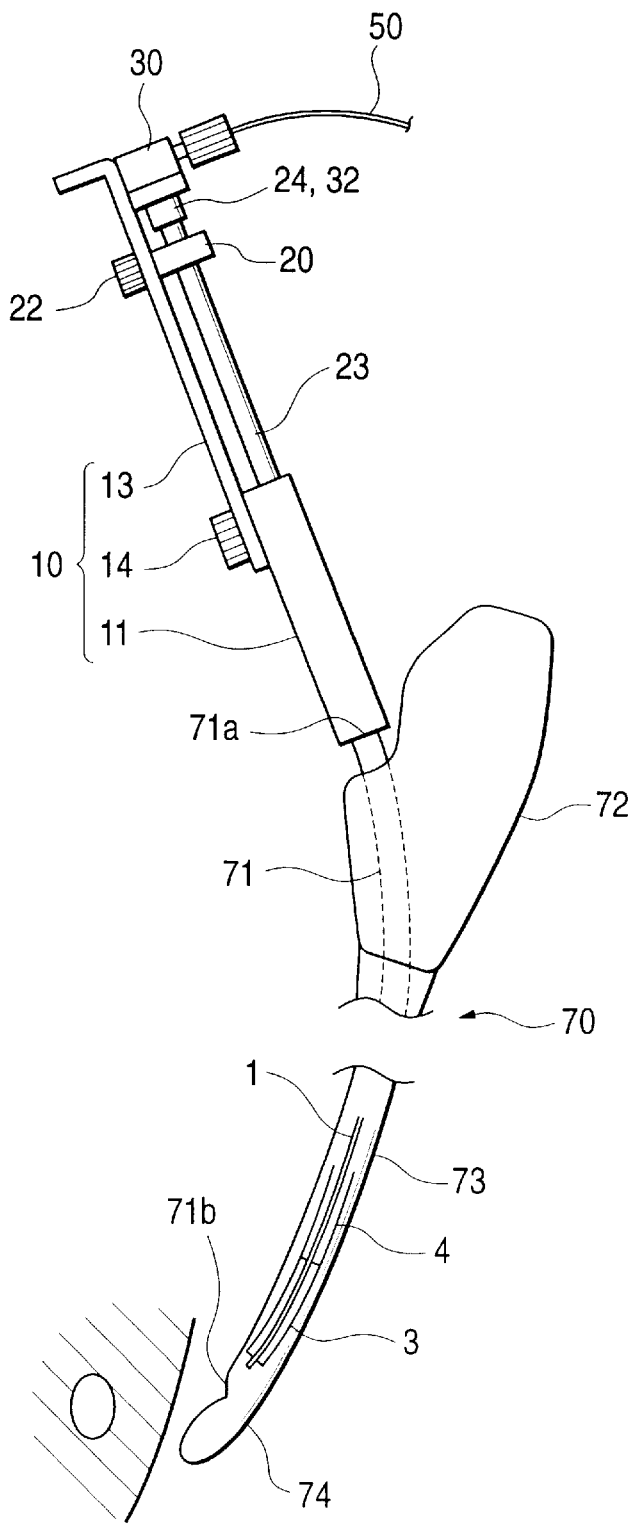
FIG. 6 is a schematic view showing a usage state of the endoscopic drainage tube holder according to the first embodiment of the present invention.

As shown in FIG. 6, an inlet 71a of a treating tool insertion channel 71 of an ultrasonic endoscope 70 is placed in an operating panel 72. Meanwhile, an outlet 71b of the treating tool insertion channel 71 is placed in a top end portion main body 74 connecting a top end of an insertion portion 73. Then, an insertion guide 10, which is used to insert/withdraw the guide wire 1 and the pusher 4 into/from the treating tool insertion channel 71, is detachably attached to the outside of the inlet 71a of the treating tool insertion channel 71.

Returning to FIG. 1, the insertion guide 10 is constructed by connecting a long and narrow cylinder portion 11 with a plate portion 13, on which a guide groove 12 is formed, using a connecting screw 14. The cylinder portion 11 is engaged attachably/detachably with the inlet 71a of the treating tool insertion channel 71 by means of a so-called lure lock female cap 9. Thus, a connection angle between the cylinder portion 11 and the guide groove 12 can be arbitrarily changed by loosening the connecting screw 14.

An axis line of the cylinder portion 11 is positioned on a projected line of an axis line of the inlet 71a of the treating tool insertion channel 71. End portions (i.e., base portions) on this side of the guide wire 1 and the pusher 4, both being inserted/withdrawn into/from the treating tool insertion channel 71, are formed to be moved along the guide groove 12 (see FIG. 5) formed on the plate portion 13.

An external thread rod 21 is projected laterally from an electrical insulating pusher base portion 20 to which a base portion of the pusher 4 is attached. The external thread rod 21 is passed through the guide groove 12, and a pusher fixing screw 22 is engaged with a top end portion of the external thread rod 21. The pusher fixing screw 22 can be tightened/loosened using the tip of a finger.

Accordingly, the pusher base portion 20 can be secured to the insertion guide 10 by tightening the pusher fixing screw 22, so that the pusher 4 can be secured to the ultrasonic endoscope 70. Conversely, the pusher 4 can be moved relative to the treating tool insertion channel 71 along its insertion/extraction direction by loosening the pusher fixing screw 22.

A reinforcing pipe 23 is coated on an exposed portion of the pusher 4 so as to prevent the buckling of the side portion of the pusher 4 due to the insertion/extraction operation. A top end of the reinforcing pipe 23 reaches the inside of the cylinder portion 11.

A connector 31 for connecting a high frequency power supply cord 50, which is connected to a high frequency power supply for cauterization, is formed on an electrical insulating guide wire base portion 30. A base portion 1c of the guide wire 1 is fitted to the connector 31. The guide wire 1 is connected to a connection terminal 31a of the connector 31. Therefore, a high frequency current can be supplied to the pricker 1a at a top end of the guide wire 1 via the guide wire 1.

The connection terminal 31a is screwed into the guide wire base portion 30 so as to push and fix the base portion 1c of the guide wire 1 at its top end. Accordingly, the guide wire 1 and the guide wire base portion 30 can be separated from each other by loosening the connection terminal 31a with respect to the guide wire base portion 30. It is preferable that a conductive metal cap be secured integrally to the base portion 1c of the guide wire 1. It is also preferable that a circumferential groove with which the top end of the connection terminal 31a is engaged be formed on an outer peripheral surface of the guide wire 1.

The guide wire 1 is inserted into the pusher 4 via a front cap 24 formed on the pusher base portion 20. This front cap 24 is formed like a lure lock male cap. A lure lock engaging female cap 32, which can be engaged with the lure lock male cap 24, is provided on the guide wire base portion 30.

Therefore, the guide wire base portion 30 and the pusher base portion 20 are moved together, with the female cap 32 engaged with the male front cap 24. If the engaging female cap 32 is disengaged from the male front cap 24, the guide wire base portion 30 and the pusher base portion 20 are brought into their mutually independent moving states. Thus, the guide wire base portion 30 can be removed from the insertion guide 10.

Figure 5:
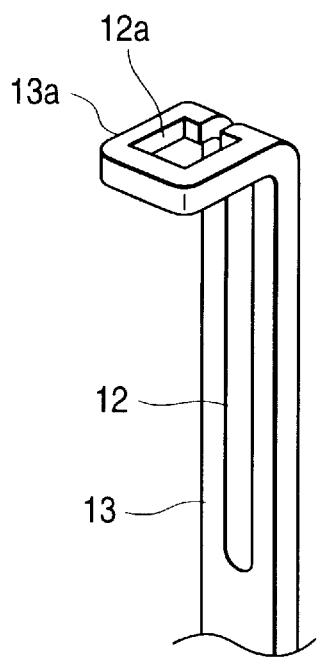
FIG. 5 is a fragmental perspective view showing an insertion guide of the endoscopic drainage tube holder according to the first embodiment of the present invention.

As shown in FIG. 5, a top end portion 13a of the plate portion 13, which is formed in an L-shape, it the short end and is bent in a lateral direction. A hole 12a through which the pusher fixing screw 22 can be passed is bored in the top end portion 13a.

The hole 12a is connected to the guide groove 12, and the pusher base portion 20 can be removed from the plate portion 13 by passing the external thread rod 21 and the pusher fixing screw 22 through the hole 12a. Nevertheless, the L-shaped top end portion 13a is closed from the outside, and thus its strength can be ensured.

In order to utilize the endoscopic drainage tube holder according to the first embodiment as described above, at first, as shown in FIG. 6, the pusher base portion 20 is engaged with the guide wire base portion 30. When both top ends of the guide wire 1 and the drainage tube 3 are positioned just on the inside of the outlet 71b of the treating tool insertion channel 71, the pusher base portion 20 can be fixed to the insertion guide 10 by the pusher fixing screw 22.

Figure 7:
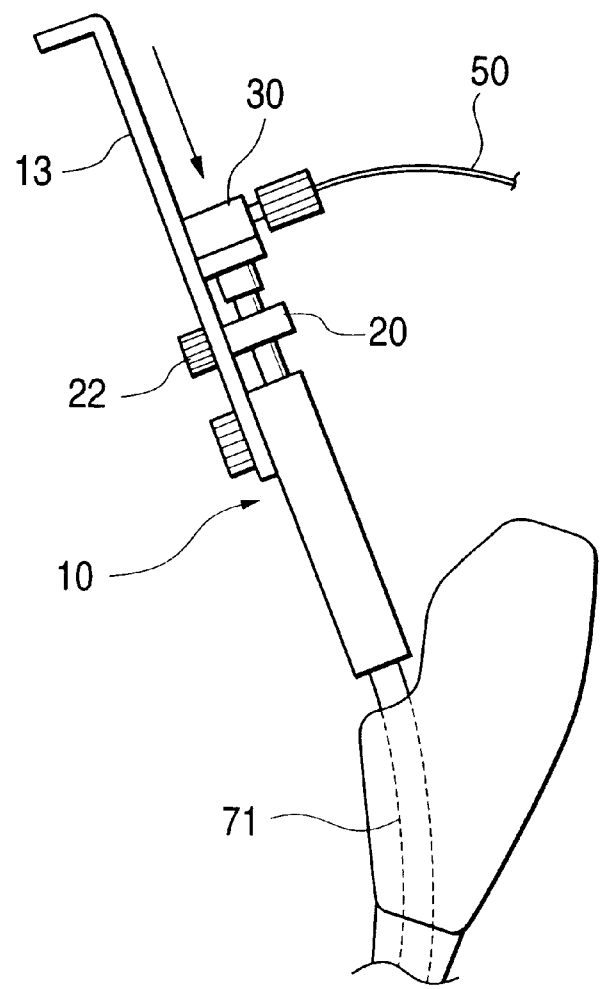
FIG. 7 is a schematic view showing another usage state of the endoscopic drainage tube holder according to the first embodiment of the present invention.
Figure 7:
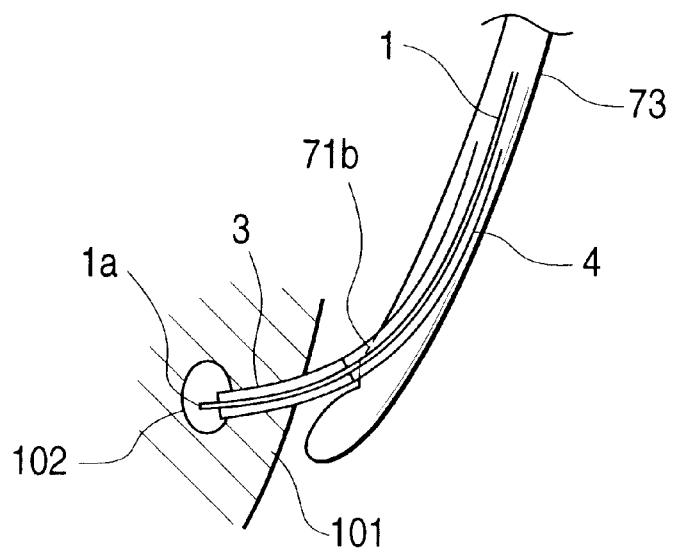

Then, as shown in FIG. 7, after loosening the pusher fixing screw 22, the pusher base portion 20 and the guide wire base portion 30 can be pushed down together from this side while supplying the high frequency current via the high frequency power supply cord 50.

At that time, the pricker 1a of the guide wire 1 is protruded forward from the outlet 71b of the treating tool insertion channel 71. The pricker 1a can then prick the pancreatic duct 102 (or the biliary duct) via the stomach wall 101 (or the duodenum wall), while burning out and solidifying the tissue of the human body. Further, the top end of the drainage tube 3 can come up to the pancreatic duct 102.

Figure 8:
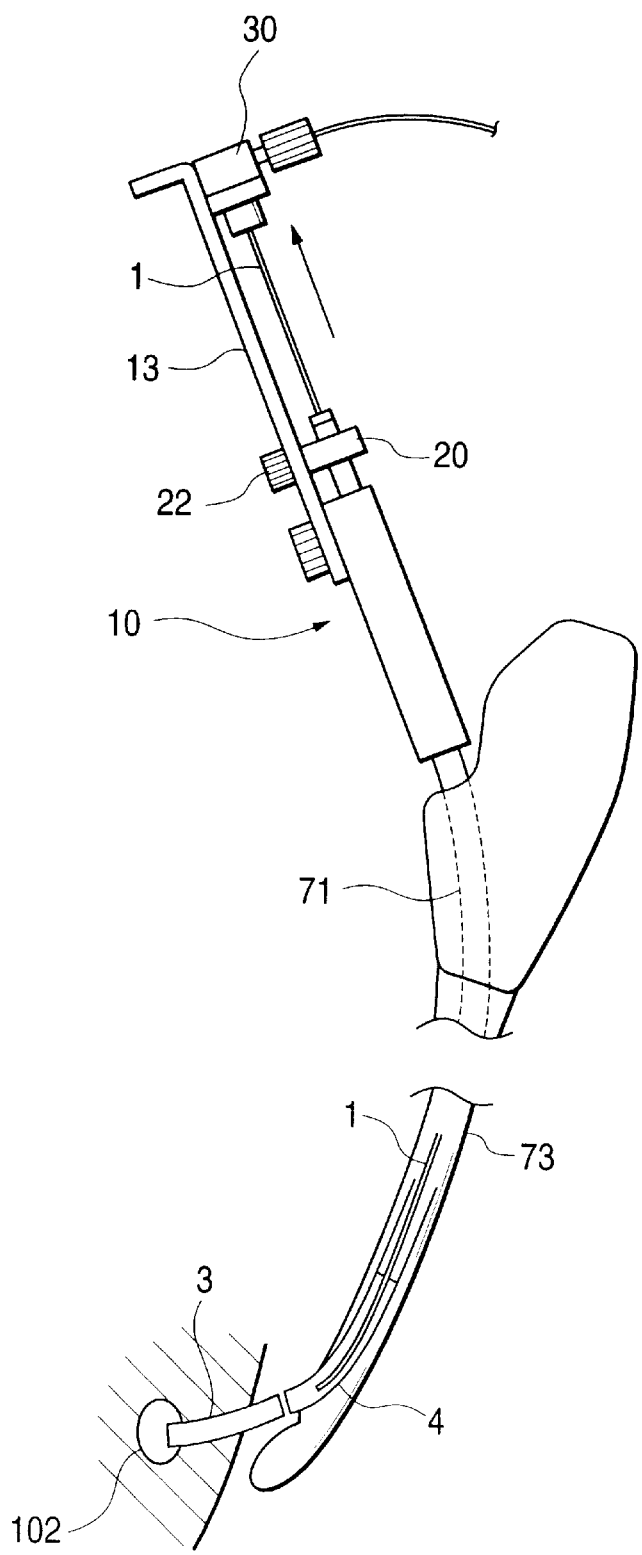
FIG. 8 is a schematic view showing still another usage state of the endoscopic drainage tube holder according to the first embodiment of the present invention.

After the drainage tube 3 has been positioned in the pancreatic duct 102, the pusher base portion 20 can be disengaged from the guide wire base portion 30. The guide wire base portion 30 can then be pulled back, as shown in FIG. 8, leaving the pusher base portion 20 fixed to the insertion guide 10.

Figure 9A:
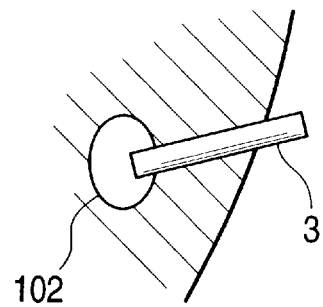
FIGS. 9A and 9B are schematic views showing the endoscope drainage tube in its held state.
Figure 9B:
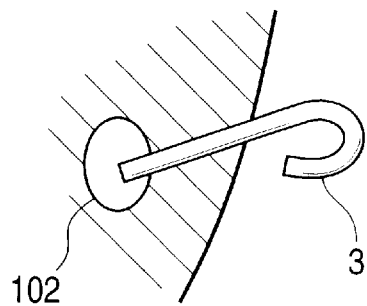
Figure 9B:
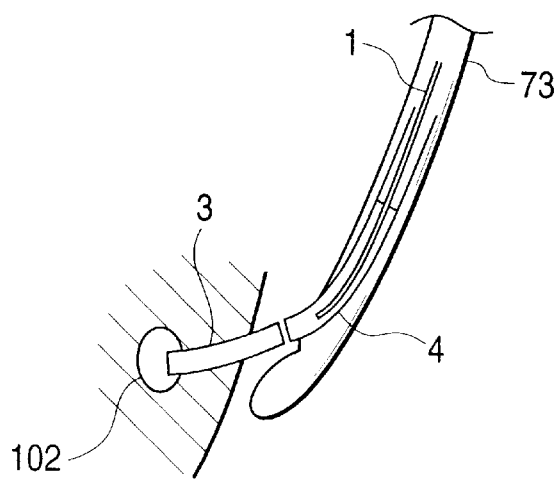

Then, if the top end of the guide wire 1 is removed from the drainage tube 3, the drainage tube 3 can be held as a single body in the body cavity, as shown in FIGS. 9A and 9B, and cardinal humors in the pancreatic duct 102 can be exhausted. In particular, FIG. 9A shows the use of a straight drainage tube 3, and FIG. 9B shows the use of a pigtail type drainage tube 3.

If the first endoscopic drainage tube holder is employed in this manner, the drainage tube 3 can be pushed in a forward direction by the pusher 4, and will not move in a backward direction when the guide wire 1 is pulled out from the drainage tube 3. The set state of the drainage tube 3 will not be disturbed, and the drainage tube 3 can be held at a correct position without fail. Therefore, an endoscope operator can easily execute a series of operations by himself.

After this drainage tube holder has been employed, the guide wire base portion 30 and the guide wire 1 can be independently separated from other tools in order to irrigate or sterilize. In addition, since the guide wire 1, which is consumed more quickly than other parts because of the high frequency current, can be replaced, the endoscopic drainage tube holder can be economically utilized.

Further, the pusher base portion 20 can be removed from the insertion guide 10 by loosening the pusher fixing screw 22. Then the pusher base portion 20 and the pusher 4 can be independently separated from other parts for irrigation/sterilization. The insertion guide 10 can also be removed from the operating panel 72 of the ultrasonic endoscope 70 to thus irrigate/sterilize independently.

Figure 10:
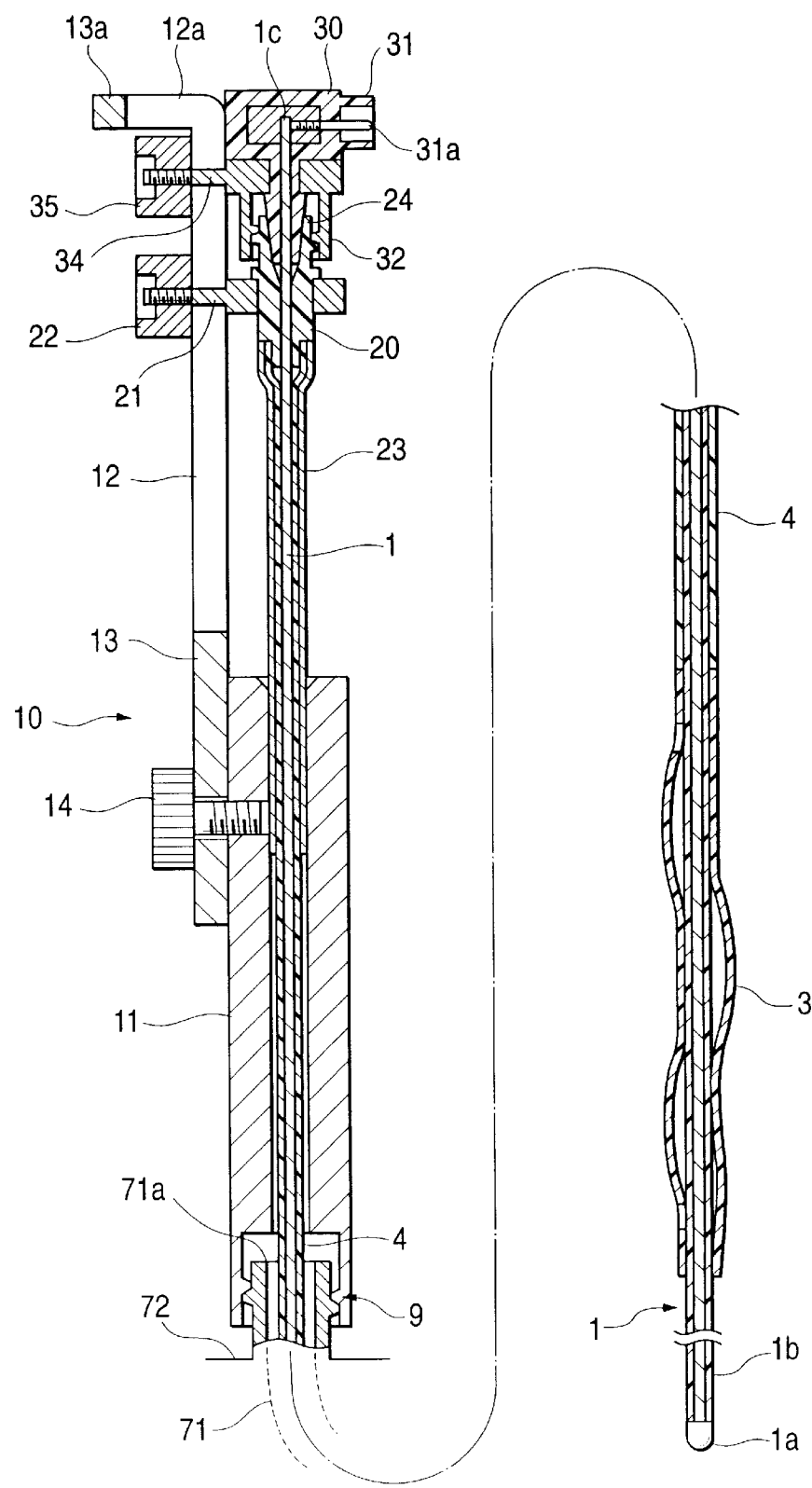
FIG. 10 is a side sectional view showing an endoscopic drainage tube holder according to a second embodiment of the present invention.

FIG. 10 shows an endoscopic drainage tube holder according to a second embodiment of the present invention. In this drainage tube holder, an external thread rod 34 and a guide wire fixing screw 35 are provided on the guide wire base portion 30, so that the guide wire base portion 30 can be fixed to the insertion guide 10. The external thread rod 34 is passed through the guide groove 12 in the same way as the pusher base portion 20, and the guide wire fixing screw 35 engages with the external thread rod 34.

The top end of the guide wire 1 of this second embodiment is formed to be a little longer than the guide wire of the first embodiment. However, other parts are identical in configuration to those of the endoscopic drainage tube holder of the first embodiment.

Figure 11:
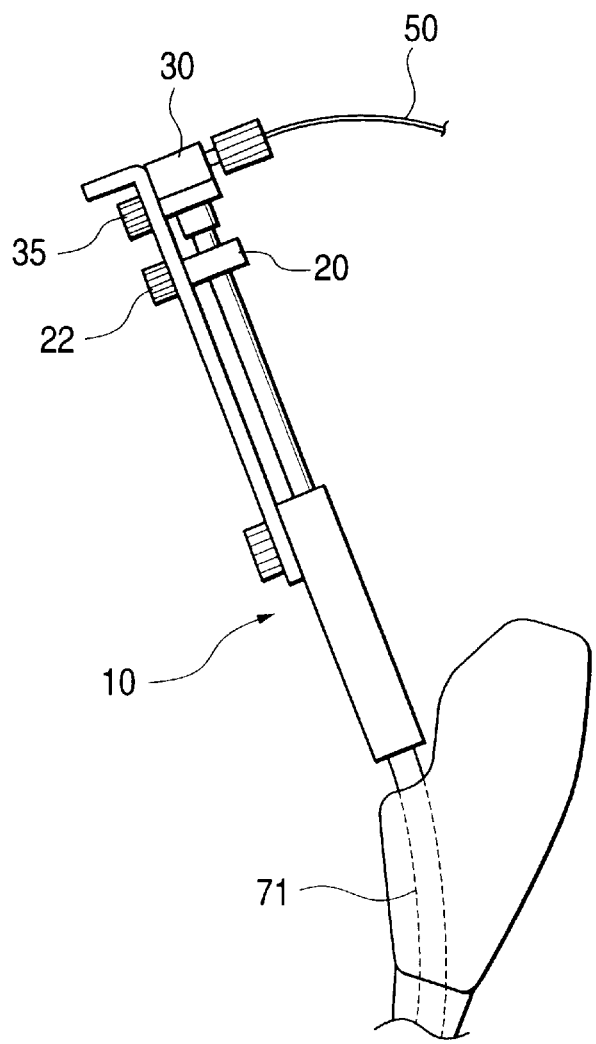
FIG. 11 is a schematic view showing a usage state of the endoscopic drainage tube holder according to the second embodiment of the present invention.
Figure 12:
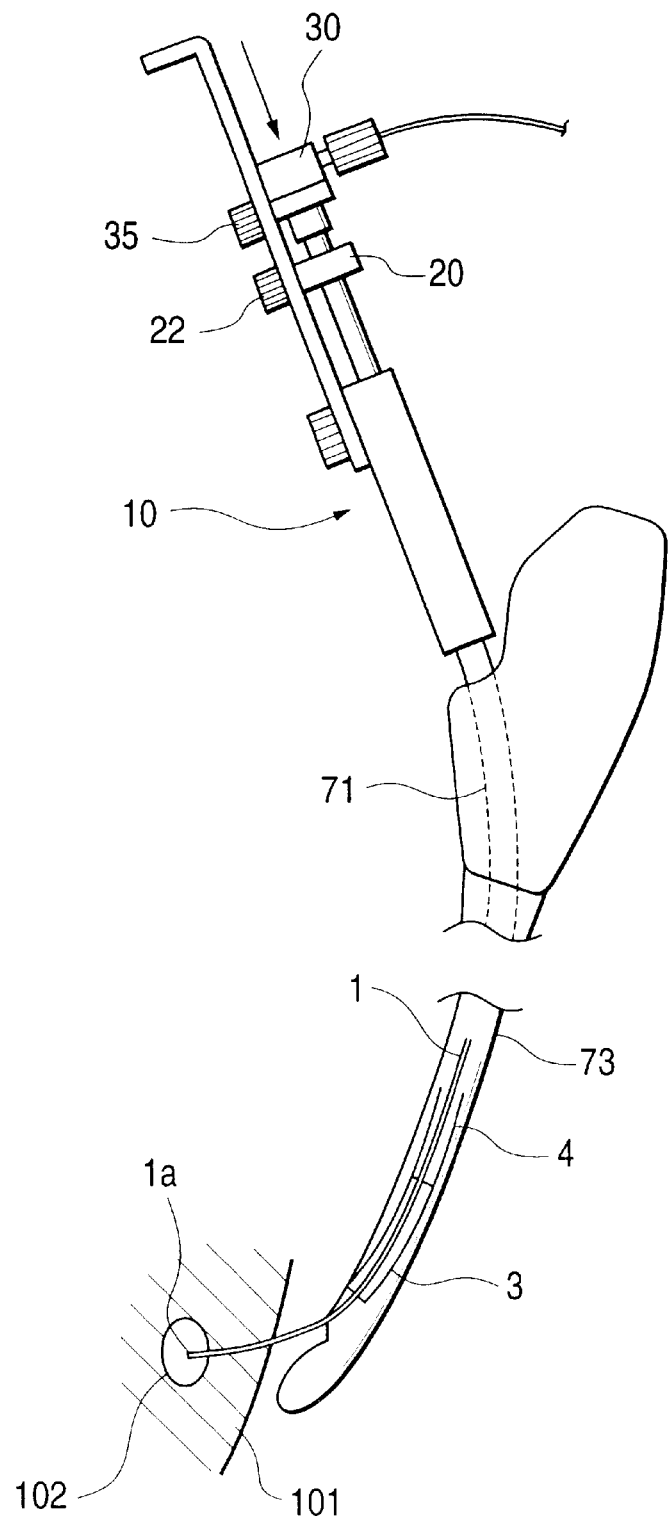
FIG. 12 is a schematic view showing another usage state of the endoscopic drainage tube holder according to the second embodiment of the present invention.

In the case of the endoscopic drainage tube holder of this second embodiment, only the guide wire 1 is first pricked into the pancreatic duct 102, as shown in FIG. 12. This is accomplished by pushing together the guide wire base portion 30 and the pusher base portion 20, both being engaged with each other, from a preparatory state shown in FIG. 11.

Figure 13:
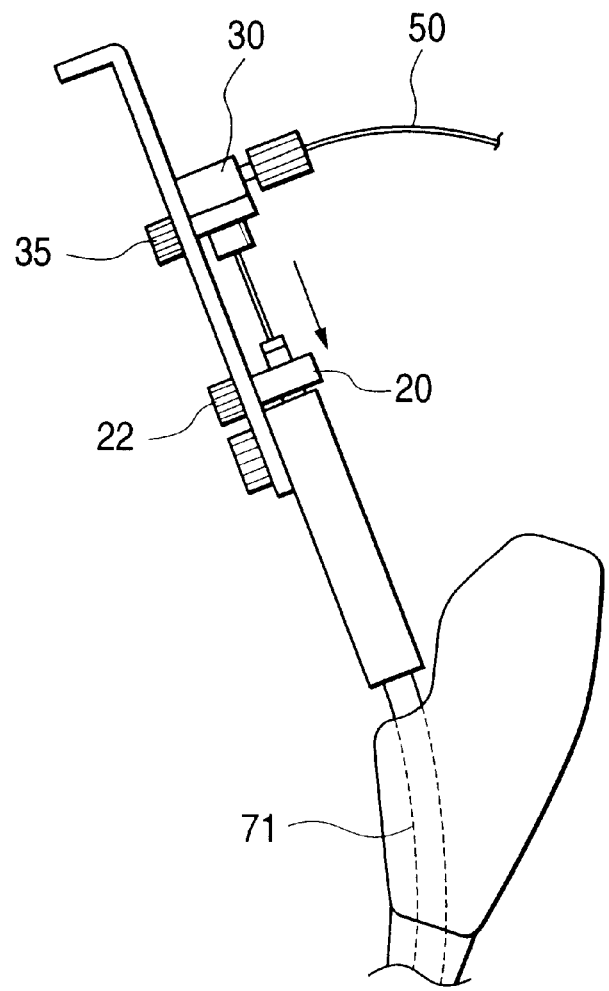
FIG. 13 is a schematic view showing still another usage state of the endoscopic drainage tube holder according to the second embodiment of the present invention.
Figure 13:
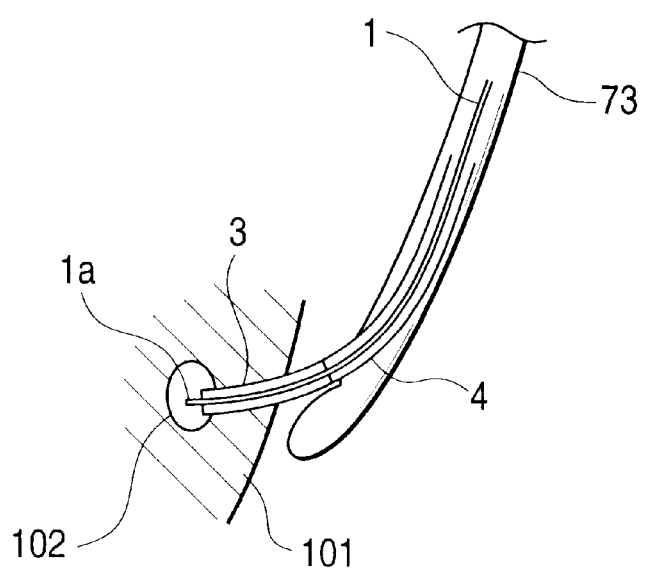

Then, as shown in FIG. 13, the guide wire base portion 30 is disengaged from the pusher base portion 20. The guide wire base portion 30 is then fixed to the insertion guide 10 by tightening the guide wire fixing screw 35, and then merely the pusher base portion 20 is pushed forward. As a result, the drainage tube 3 can reach the pancreatic duct 102, using the guide wire 1 as a guide.

When the pusher fixing screw 22 is tightened and the guide wire fixing screw 35 is loosened. Then, in the same way as in the endoscopic drainage tube holder of the first embodiment shown in FIG. 8, the guide wire base portion 30 is pulled back while fixing the pusher base portion 20 remains fixed to the insertion guide 10. As a result, the drainage tube 3 can be held correctly in the body cavity when the guide wire 1 is removed from the drainage tube 3.

Figure 14:
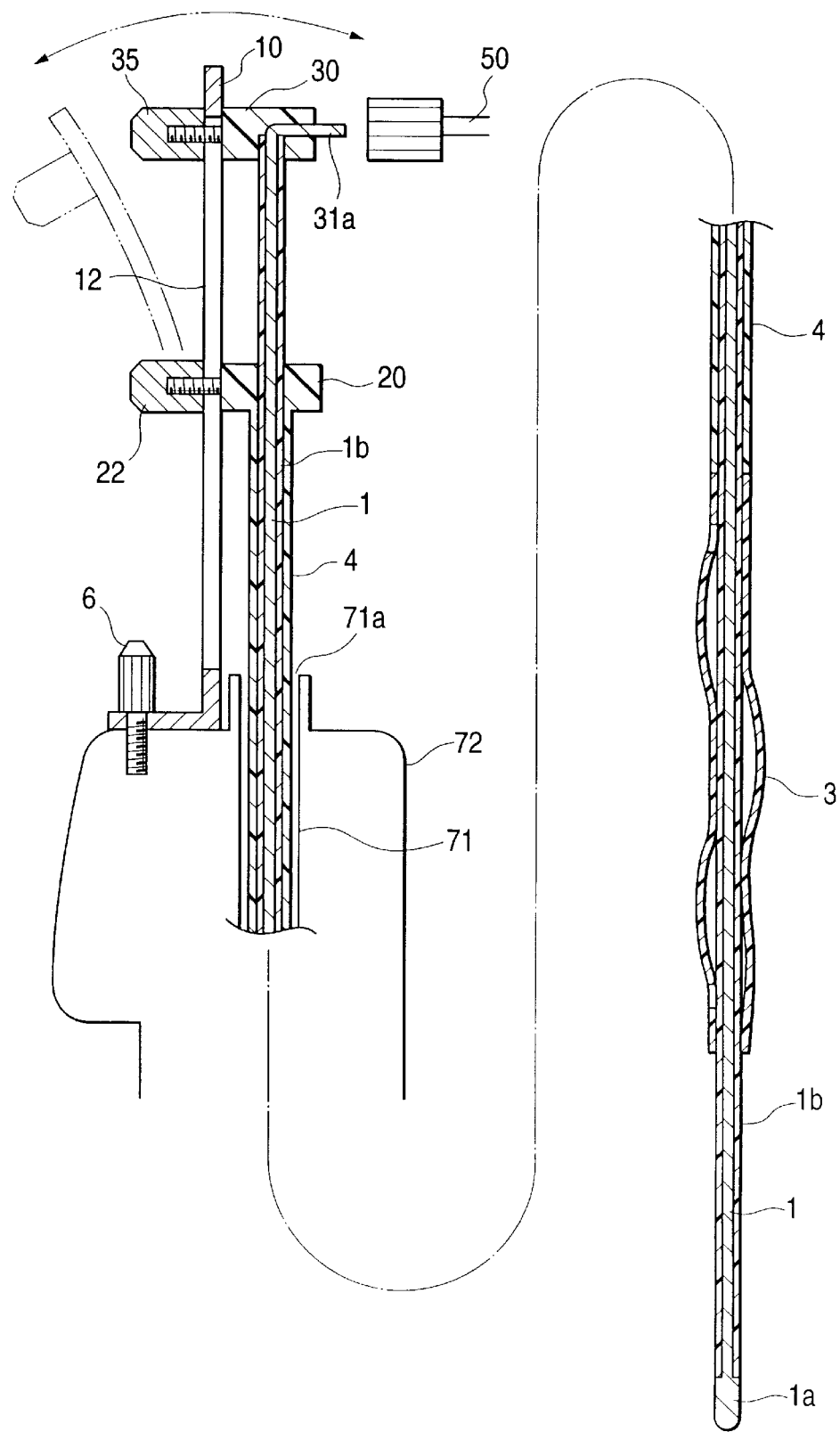
FIG. 14 is a side sectional view showing an endoscopic drainage tube holder according to a third embodiment of the present invention.

FIG. 14 shows an endoscopic drainage tube holder according to a third embodiment of the present invention. The guide wire 1, the drainage tube 3, and the pusher 4 are identical to those of the endoscopic drainage tube holder of the first embodiment, as shown in FIG. 1, and therefore their explanation will be omitted.

The insertion guide 10 for guiding the endoscopic drainage tube holder into the treating tool insertion channel 71 can be maintained in an upright position. This is accomplished by using a fixing screw 6 on the outside of the inlet 71a of the treating tool insertion channel 71 into which the endoscopic drainage tube holder is inserted.

Figure 15:
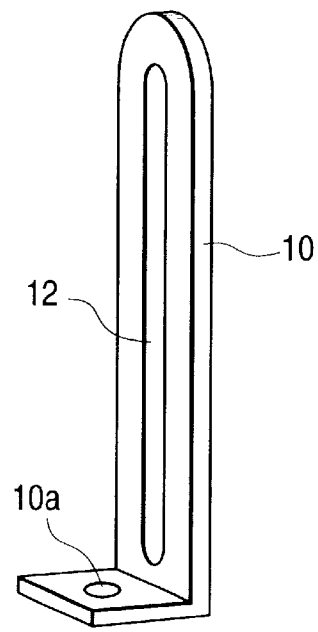
FIG. 15 is a perspective view showing an insertion guide of the third embodiment of the present invention.

As shown in FIG. 15, the insertion guide 10 is formed by bending a plate member in an L-shape, and the straight, long and narrow guide groove 12 is formed in the insertion guide 10. Reference numeral 10a indicates a hole through which the fixing screw 6 is passed.

Returning to FIG. 14, the insertion guide 10, when fitted to the operating panel 72 of the endoscope, is arranged such that the guide groove 12 is positioned near the inlet 71a of, and in parallel with the axis of, the treating tool insertion channel 71. Hence, both the guide wire 1 and the pusher 4, which are inserted/extracted into/from the treating tool insertion channel 71, are moved along the guide groove 12.

Then, an external thread rod, which is projected laterally from the electrical insulating pusher base portion 20 formed on the base portion of the pusher 4, is passed through the guide groove 12. The pusher fixing screw 22 is engaged with a top end portion of the external thread rod. Therefore, the pusher base portion 20 can be fixed to the insertion guide 10, to thus bring the pusher 4 into its fixed state if the pusher fixing screw 22 is tightened. Meanwhile, the pusher 4 can be moved relative to the treating tool insertion channel 71 in the insertion/extraction direction if the pusher fixing screw 22 is loosened.

Similarly, a base portion of the guide wire 1, which is projected further from the base portion of the pusher 4 toward this side, can also be fixed to the insertion guide 10 by the guide wire fixing screw 35. In other words, the external thread rod, which is protruded laterally from the electrical insulating guide wire base portion 30 formed on the base portion of the guide wire 1, is passed through the guide groove 12, and the guide wire fixing screw 35 is engaged with the top end of the external thread rod. Consequently, the guide wire base portion 30 can be fixed to the insertion guide 10 by tightening the guide wire fixing screw 35 to thus bring the guide wire 1 into its fixed state. Meanwhile, the guide wire 1 can be moved relative to the treating tool insertion channel 71 in the insertion/extraction direction by loosening the guide wire fixing screw 35.

If the high frequency power supply cord 50 is connected to the connection terminal 31a formed on the base portion of the guide wire 1, the high frequency current is supplied to the pricker 1a provided at the top end via the connection terminal 31a and the guide wire 1.

Figure 16:
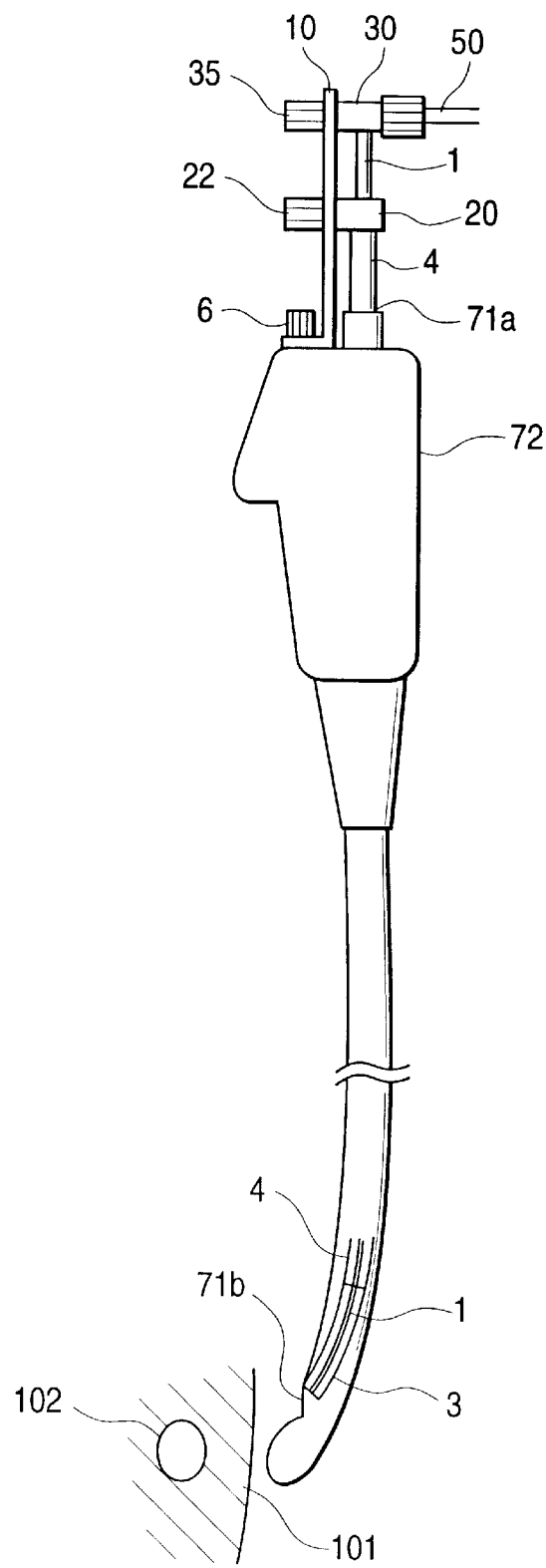
FIG. 16 is a schematic view showing a usage state of the endoscopic drainage tube holder according to the third embodiment of the present invention.

The utilization of the endoscopic drainage tube holder of the third embodiment will now be described. As shown in FIG. 16, both top ends of the guide wire 1 and the drainage tube 3 are first positioned just on the inside of the outlet 71b of the treating tool insertion channel 71. The guide wire base portion 30 and the pusher base portion 20 can be fixed to the insertion guide 10 by the pusher fixing screw 22 and the guide wire fixing screw 35. At that time, the pusher base portion 20 and the guide wire base portion 30 are each positioned along the treating tool insertion channel 71. The pusher base portion 20 is positioned in the intermediate portion of the insertion guide 10, and the guide wire base portion 30 is positioned at the top end of the insertion guide 10.

Figure 17:
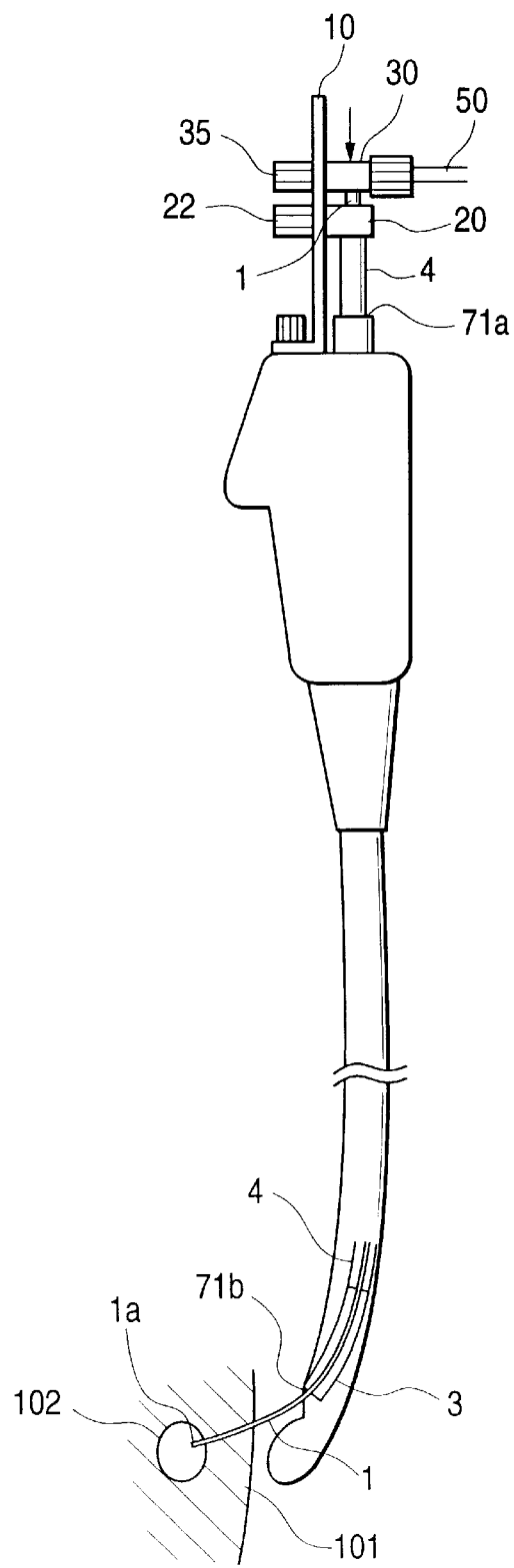
FIG. 17 is a schematic view showing another usage state of the endoscopic drainage tube holder according to the third embodiment of the present invention.

As shown in FIG. 17, when the pusher base portion 20 is fixed to the insertion guide 10, the pusher base portion 20 and the guide wire base portion 30 are pushed out from this side by loosening the guide wire fixing screw 35. Meanwhile, the high frequency current is supplied via the high frequency power supply cord 50. The pricker 1a of the guide wire 1 can then protrude forward from the outlet 71b of the treating tool insertion channel 71. Thus, while burning out and solidifying the tissue of the human body, the pricker 1a can be pricked into the pancreatic duct 102 via the stomach wall 101. At this time, the pusher 4 is not moved, because it is fixed by the pusher fixing screw 22.

The drainage tube 3 may be left in the treating tool insertion channel 71, as shown in FIG. 17. Alternatively, the drainage tube 3 may protrude slightly from the outlet 71b of the treating tool insertion channel 71 because of a frictional force between the guide wire 1 and the drainage tube 3. Either position is acceptable.

The pricking operation is continued until the guide wire base portion 30 reaches the pusher base portion 20. If a pricking depth is not sufficient, the pusher base portion 20 can be pushed out by loosening the pusher fixing screw 22 and then, after the pusher base portion 20 has been fixed by the pusher fixing screw 22 again, the guide wire base portion 30 can be pushed out again until it reaches the pusher base portion 20.

Figure 18:
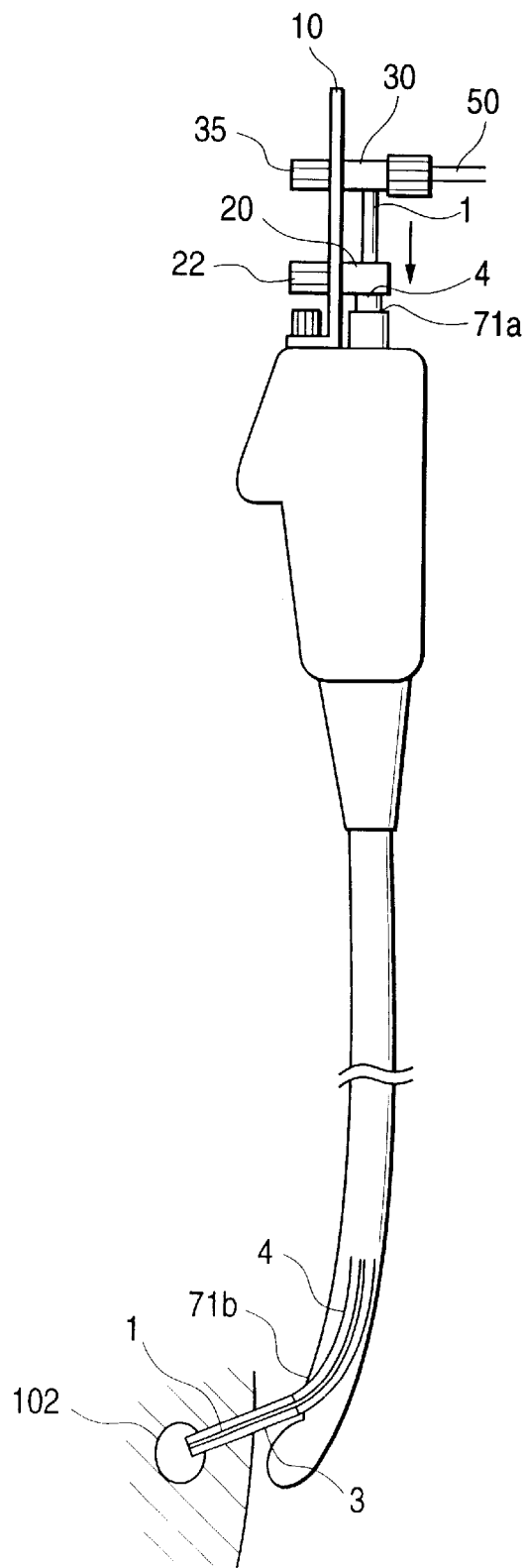
FIG. 18 is a schematic view showing still another usage state of the endoscopic drainage tube holder according to the third embodiment of the present invention.

When the pricker 1a of the guide wire 1 has been positioned in the pancreatic duct 102, as shown in FIG. 18, the guide wire base portion 30 can be fixed to the insertion guide 10 by the guide wire fixing screw 35. Then the pusher base portion 20 can be pushed out from this side by loosening the pusher base portion 20. At that time, on the outlet 71b side of the treating tool insertion channel 71, the drainage tube 3 is pushed by the pusher 4 to pass through the pricking hole formed in the stomach wall 101. Then the top end of the drainage tube 3 can reach the pancreatic duct 102. In this case, the guide wire 1 is not moved at all because it is fixed to the insertion guide 10 by the guide wire fixing screw 35.

When the drainage tube 3 is brought into the above situation, the drainage tube 3 can be held as a single body in the body cavity by pulling out the guide wire 1 as well as the pusher 4. The pancreatic juice in the pancreatic duct 102 can then be exhausted into the stomach. Further, the endoscope operator can easily carry out a series of operations, without assistance.

After this drainage tube holder has been employed, the guide wire 1 and the pusher 4 can be removed independently from the insertion guide 10 by loosening the pusher fixing screw 22 and the guide wire fixing screw 35, respectively. Therefore, they can irrigate/sterilize every nook and corner. In addition, since the guide wire 1 side members, which are consumed more quickly than other parts because of the high frequency current, can be replaced, the endoscopic drainage tube holder can be utilized more economically. These advantages are true of the endoscopic drainage tube holders of the embodiments described further below.

Further, if the insertion guide 10 is formed of a flexible material, it is easy to use since it can be bent appropriately in accordance with the employment circumstances, as indicated by a chain double-dashed line in FIG. 14.

Figure 19:
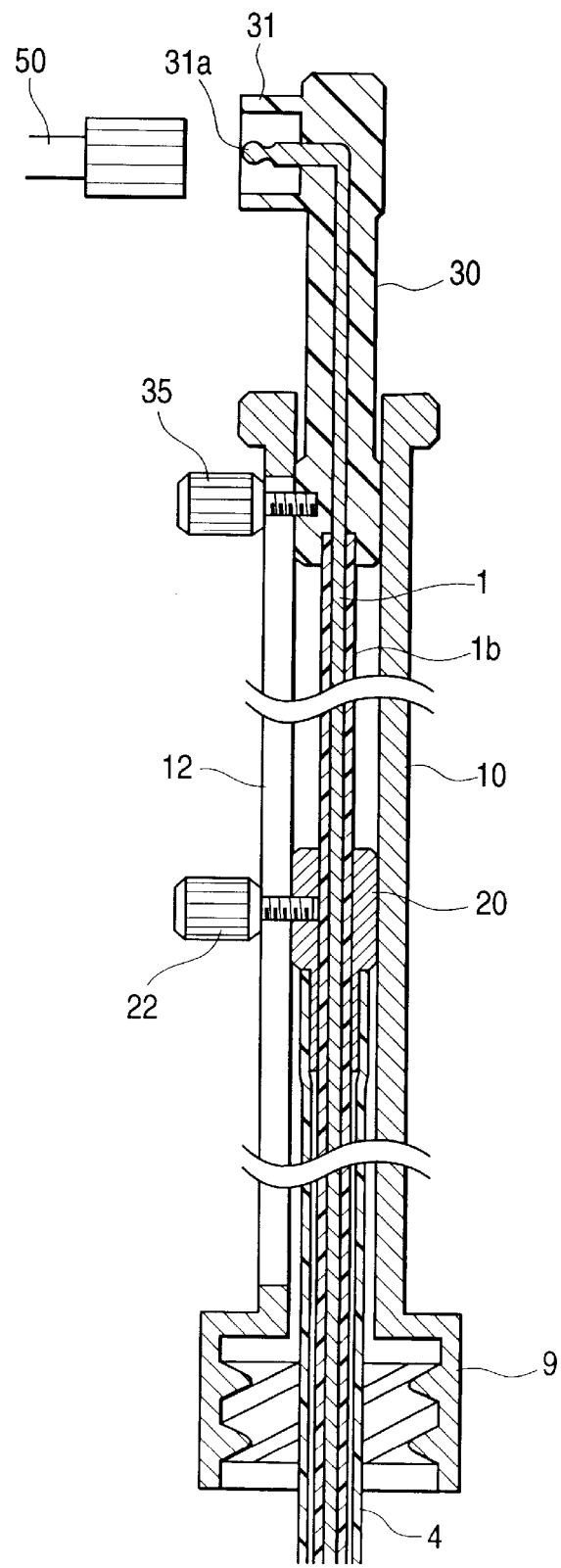
FIG. 19 is a side sectional view showing a side portion of an endoscopic drainage tube holder according to a fourth embodiment of the present invention.
Figure 20:
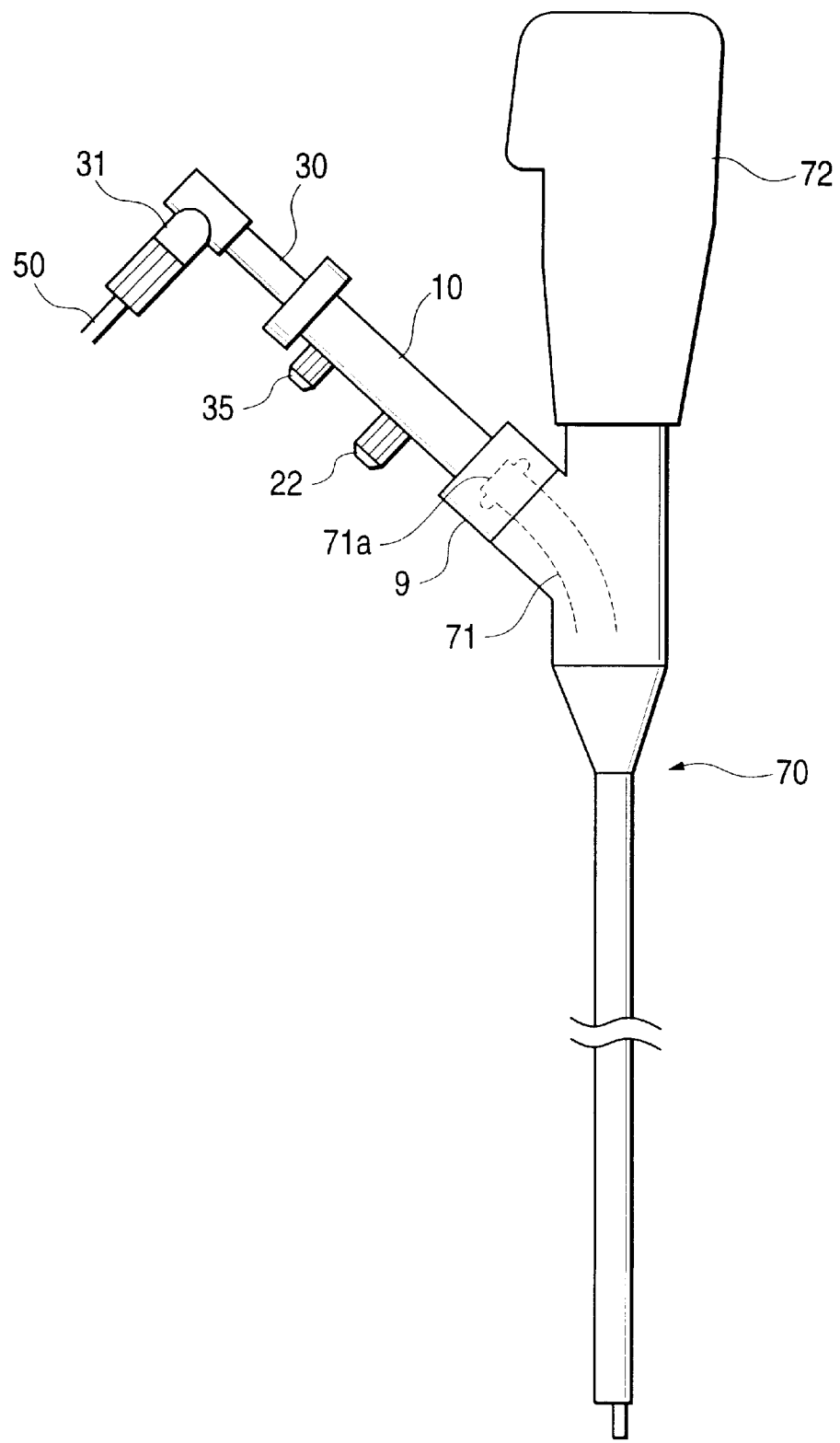
FIG. 20 is a side view showing a state in which the endoscopic drainage tube holder according to the fourth embodiment of the present invention is set in an endoscope.

FIG. 19 shows an endoscopic drainage tube holder according to a fourth embodiment of the present invention. The insertion guide 10 is formed in a cylindrical shape, and then a so-called lure lock female cap 9 is formed at the end portion of the insertion guide 10. As a result, as shown in FIG. 20, the insertion guide 10 can be coupled/released into/from the outlet 71a side of the treating tool insertion channel 71.

Except for the pusher base portion 20 and the guide wire base portion 30 being respectively formed in a rod-like shape so as to be slidingly fitted into the insertion guide 10, other parts as well as their operations are similar to those in the endoscopic drainage tube holder of the third embodiment.

Figure 21:
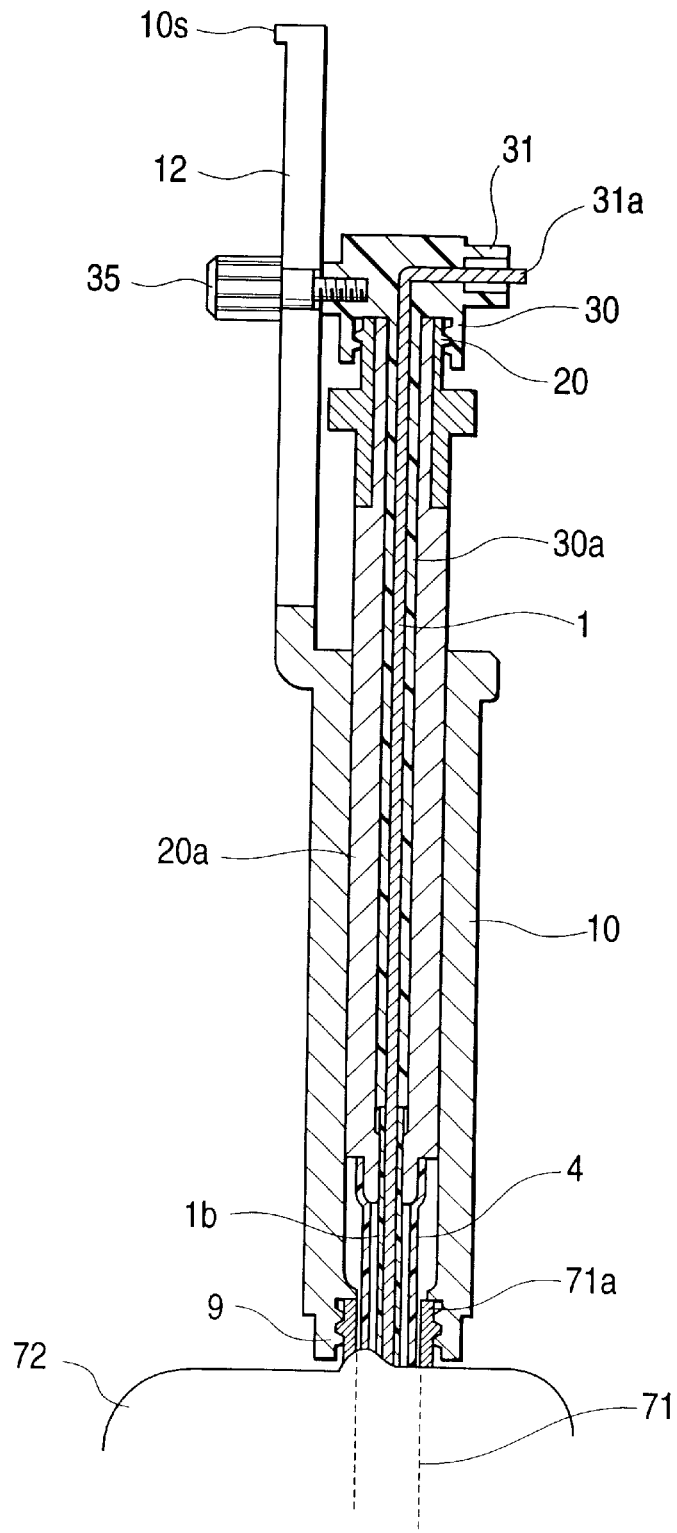
FIG. 21 is a side sectional view showing a side portion of an endoscopic drainage tube holder according to a fifth embodiment of the present invention.

FIG. 21 shows an endoscopic drainage tube holder according to a fifth embodiment of the present invention. Only the guide wire base portion 30 provided at the base end of the guide wire 1 can be fixed at any position on the guide groove 12 of the insertion guide 10 by the guide wire fixing screw 35. The pusher base portion 20 provided at the base end of the pusher 4 can be coupled/released into/from the guide wire base portion 30 by using a lure lock cap structure.

A half of the insertion guide 10 near the operating panel 72 of the endoscope is formed in a cylindrical shape, as in the endoscopic drainage tube holder of the fourth embodiment. The insertion guide 10 is then attachably/detachably coupled to the inlet 71a of the treating tool insertion channel 71 by the lure lock female cap 9. A half of the insertion guide 10 on the remote side from the operating panel 72 is formed in a plate-like shape, as in the endoscopic drainage tube holder of the first embodiment; the guide groove 12 is formed on this half of the insertion guide 10. A reference 10s denotes a stopper that can prevent the guide wire fixing screw 35 from being pulled out from the guide groove 12.

A coupling cylinder 20a, which is fitted loosely into the insertion guide 10 so as to be rotatable and slidable along the axial line therein, is interleaved/connected between the base portion of the pusher 4 and the pusher base portion 20. The pusher base portion 20 is coupled with the coupling cylinder 20a rotatably around the axis line.

Accordingly, the pusher base portion 20 can be easily coupled/released into/from the guide wire base portion 30. Also, a coupling pipe 30a, which is fitted loosely into the coupling cylinder 20a, is interleaved/connected between the base portion of an insulating jacket 1b of the guide wire 1 and the guide wire base portion 30.

Figure 22:
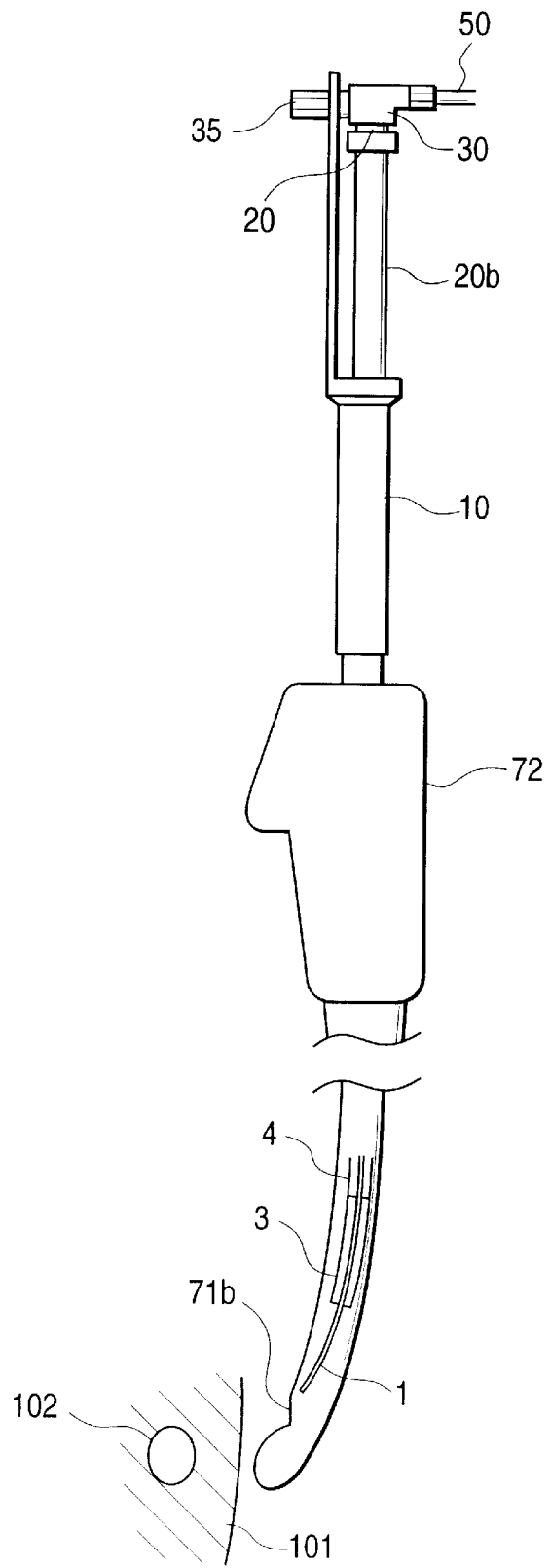
FIG. 22 is a schematic view showing a usage state of the endoscopic drainage tube holder according to the fifth embodiment of the present invention.

The utilization of the endoscopic drainage tube holder of the fifth embodiment will now be described. The pusher base portion 20 and the guide wire base portion 30 are coupled with each other. Then the guide wire fixing screw 35 is screwed/fixed into/to the insertion guide 10 when the top end of the guide wire 1 is protruded from the top end of the drainage tube 3, as shown in FIG. 22.

Figure 23:
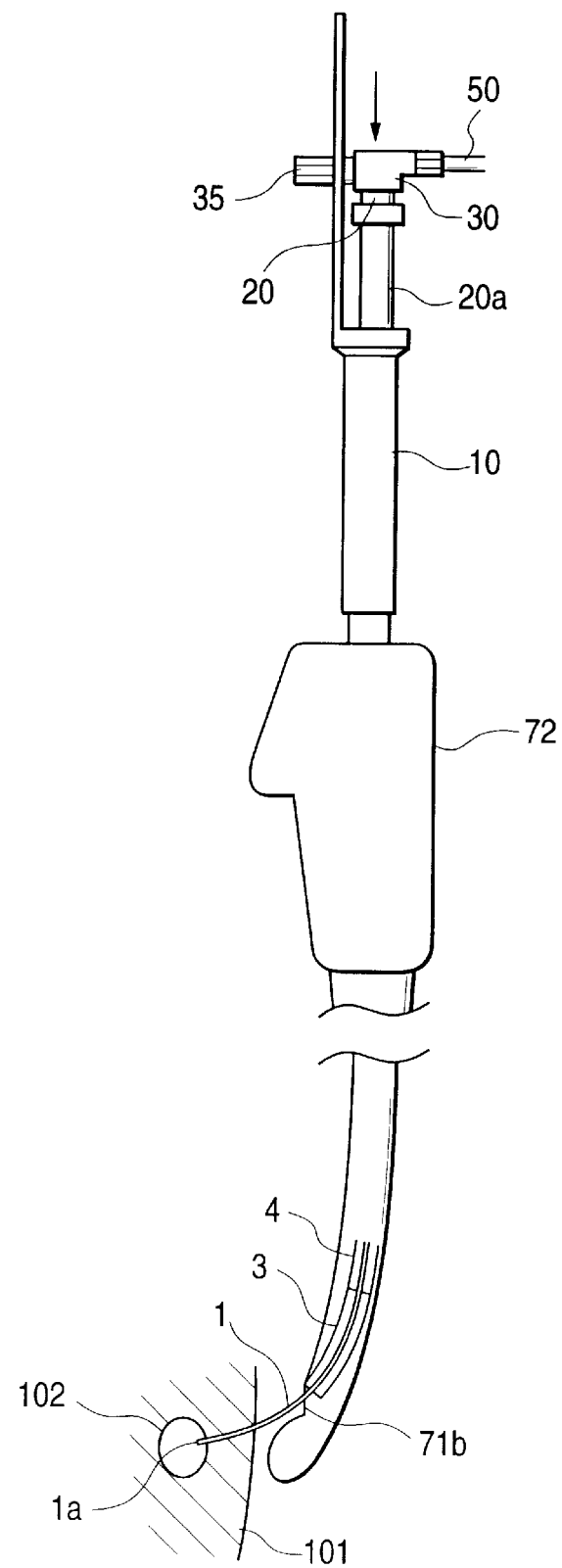
FIG. 23 is a schematic view showing another usage state of the endoscopic drainage tube holder according to the fifth embodiment of the present invention.

Then, as shown in FIG. 23, when the pusher base portion 20 and the guide wire base portion 30 are still connected to each other, the pusher base portion 20 and the guide wire base portion 30 are pushed out from this side by loosening the guide wire fixing screw 35, while supplying the high frequency current to the guide wire 1. At that time, on the outlet 71b side of the treating tool insertion channel 71, the pricker 1a of the guide wire 1 is projected forwardly to prick into the pancreatic duct 102 via the stomach wall 101. At the same time, the drainage tube 3 and the pusher 4 are moved forwardly, together with the guide wire 1.

Figure 24:
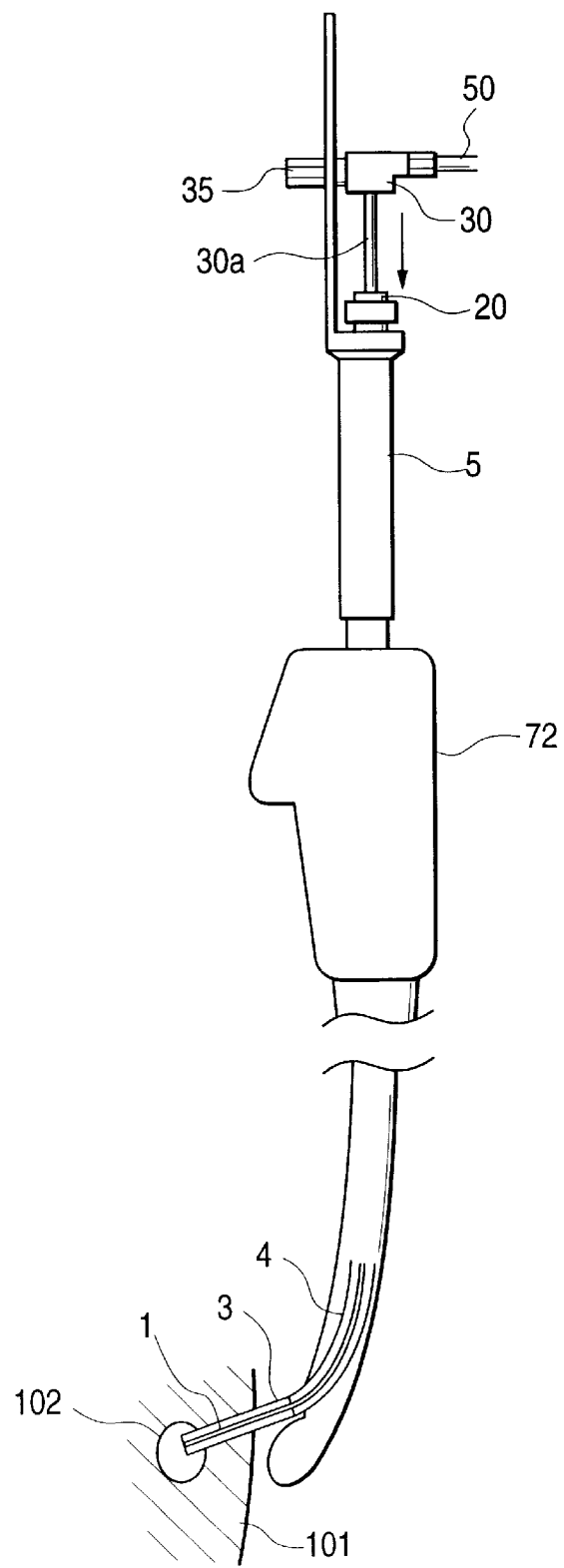
FIG. 24 is a schematic view showing still another usage state of the endoscopic drainage tube holder according to the fifth embodiment of the present invention.

When the pricker 1a of the guide wire 1 is positioned in the pancreatic duct 102, as shown in FIG. 24, the guide wire fixing screw 35 is fixed to the insertion guide 10. A coupled state of the pusher base portion 20 and the guide wire base portion 30 is released, and then only the pusher base portion 20 is pushed out from the operator side. The drainage tube 3 is then pushed forwardly from the outlet 71b of the treating tool insertion channel 71 by the pusher 4 to pass through the pricking hole formed in the stomach wall 101. The top end of the drainage tube 3 then reaches the pancreatic duct 102. However, the guide wire 1 is not moved at all at this time, because it is fixed to the insertion guide 10 by the guide wire fixing screw 35.

When the drainage tube 3 is brought into the above state, only the drainage tube 3 can be held as a single body in the body cavity by pulling out the guide wire 1 and the pusher 4 together. As a result, the pancreatic juice in the pancreatic duct 102 can be exhausted into the stomach. Further, the endoscope operator can easily carry out the series of operations, without assistance.

Figure 25:
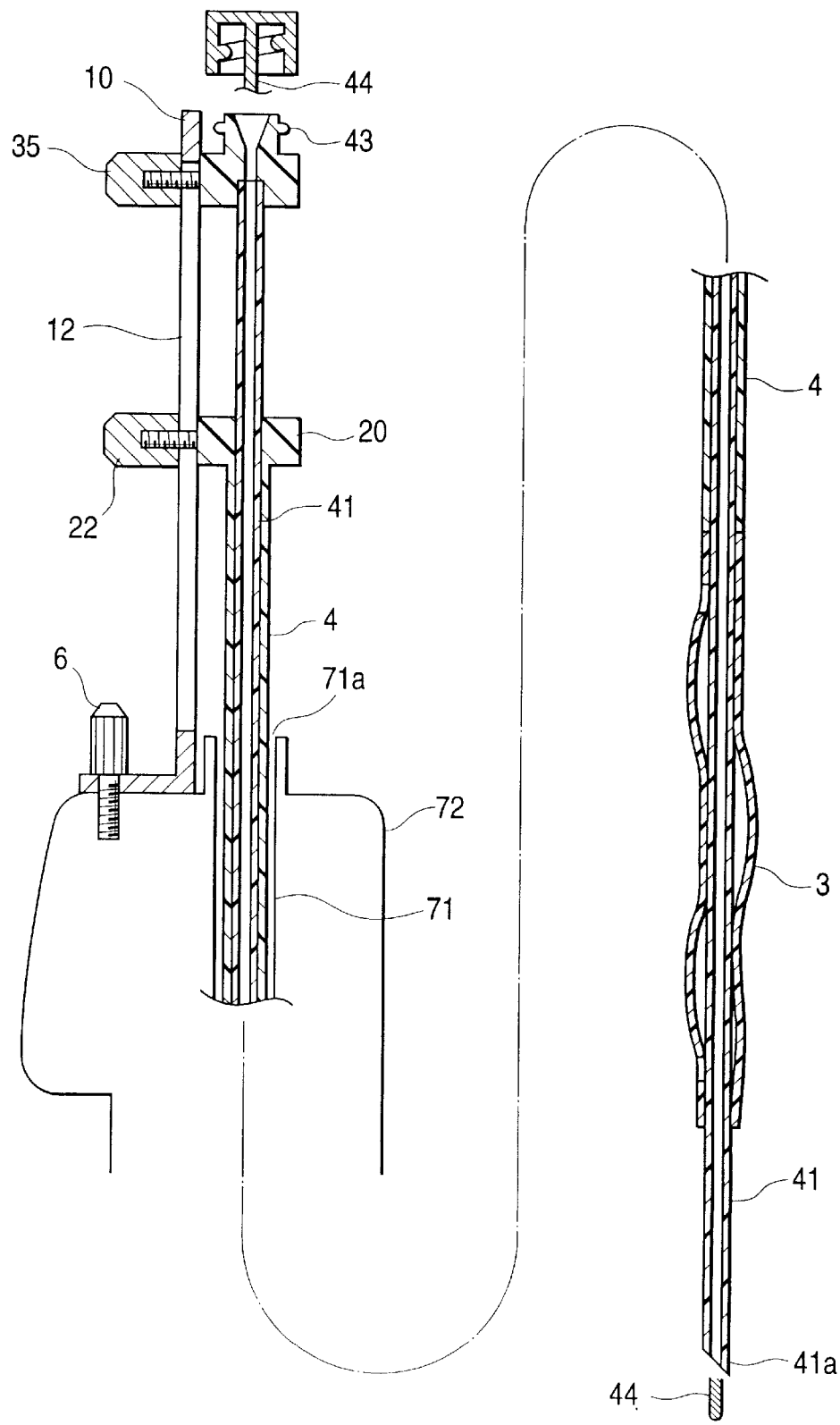
FIG. 25 is a side sectional view showing an endoscopic drainage tube holder according to a sixth embodiment of the present invention.

FIG. 25 shows an endoscopic drainage tube holder according to a sixth embodiment of the present invention. In place of the guide wire 1 of the endoscopic drainage tube holder of the third embodiment shown in FIG. 14, a flexible tube 41 is employed as a linear guiding member. A pricker 41a provided at the top end of the flexible tube 41 is formed like an injection needle.

An injection cylinder holding cap 43, which is fixed to the insertion guide 10 by the guide wire fixing screw 35, is formed to communicate with a side end portion of the flexible tube 41. Then, in a pricking operation, a core bar 44 whose length is set to protrude from the top end of the pricker 41a can be inserted into the flexible tube 41.

With such a configuration, treatments such as absorption cell diagnosis, injection, etc. can be carried out by piercing the pricker 41a into the tissue and pulling out the core bar 44. A holding treatment of the drainage tube 3 can subsequently be accomplished.

Figure 26:
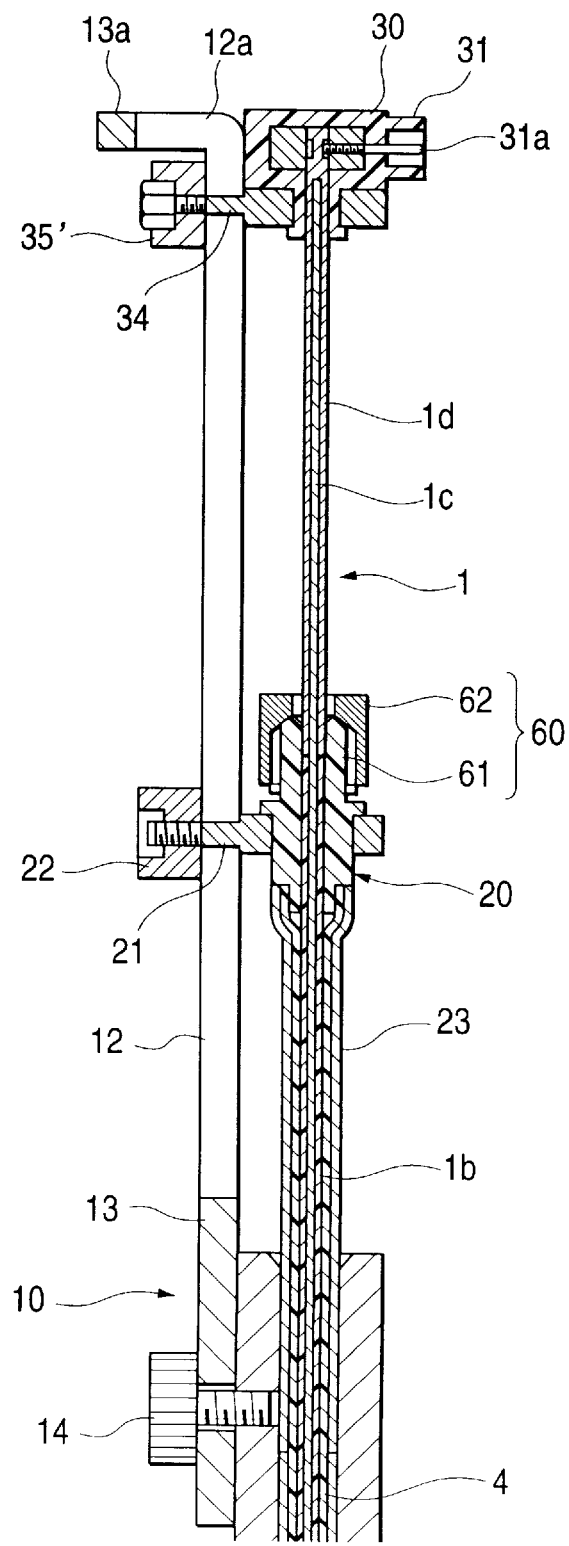
FIG. 26 is a side sectional view showing an endoscopic drainage tube holder according to a seventh embodiment of the present invention.

FIG. 26 shows an endoscopic drainage tube holder according to a seventh embodiment of the present invention. Only the pusher base portion 20 can be manually fixed to the insertion guide 10 by the pusher fixing screw 22. Simultaneously, a guide wire fixing screw 60, used to arbitrarily fix/release the guide wire 1, is provided to the pusher base portion 20. Other configurations are identical to those in the endoscopic drainage tube holder of the first embodiment.

A coming-off prevention screw 35', which is attached to the guide wire base portion 30, is fixed by a double nut so as not to touch the plate portion 13 of the insertion guide 10. More particularly, the coming-off prevention screw 35' is fixed so that the guide wire base portion 30 does not move out of position parallel with the plate portion 13, without having to fix the guide wire base portion 30 to the plate portion 13.

Figure 27:
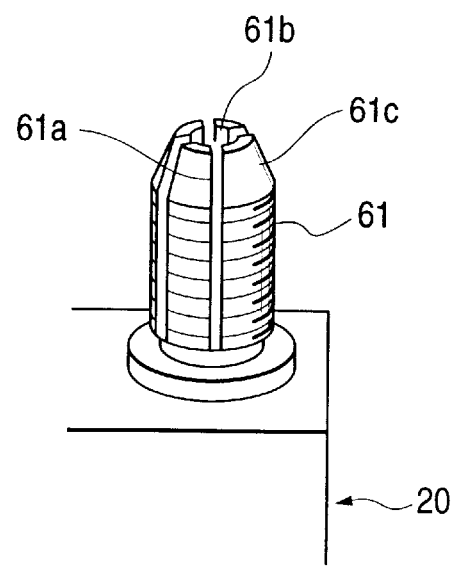
FIG. 27 is a perspective view showing a chuck screw employed in the seventh embodiment of the present invention.

The guide wire fixing screw 60 includes a chuck screw 61, which is formed integrally with the pusher base portion 20, and a fastening nut 62, which is externally engaged with the chuck screw 61. As shown in FIG. 27, the chuck screw 61 is split by four slots 61a positioned at 90° intervals and in parallel with the axis of the chuck screw 61. A through hole 61b, through which the guide wire 1 is loosely passed, is formed on the axis, and a top end surface is formed as a tapered surface 61c.

A tapered surface, which contacts to the tapered surface 61c of the chuck screw 61, is formed on an inner surface of the fastening nut 62. Therefore, the chuck screw 61 is deformed to be moved inwardly by fastening the fastening nut 62, so that the guide wire 1, which is passed through the inner through hole 61b, is fixed to the chuck screw 61 (i.e., the pusher base portion 20). Conversely, the fixing state of the guide wire 1 can be released by loosening the fastening nut 62, so that the guide wire 1 becomes independent from the pusher base portion 20 to be moved back and forth.

The insulating jacket 1b covers the full length of the guide wire 1. Further, a reinforcing metal pipe 1d covers a portion of the guide wire 1 exposed out of the pusher 4.

Figure 28:
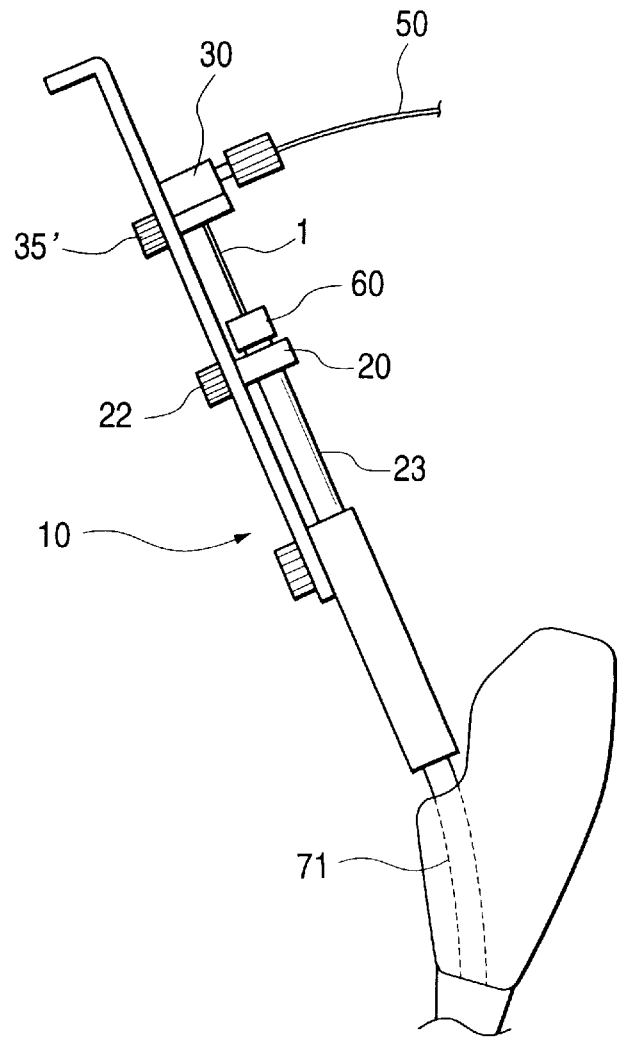
FIG. 28 is a schematic view showing a usage state of the endoscopic drainage tube holder according to the seventh embodiment of the present invention.
Figure 28:
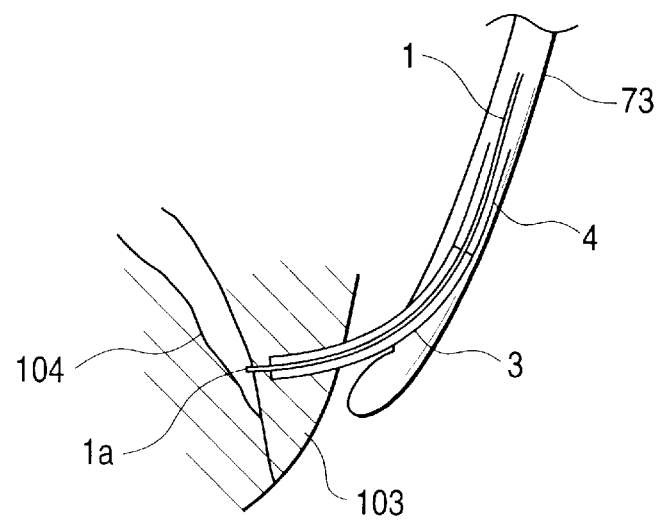

The utilization of the endoscopic drainage tube holder of the seventh embodiment will now be described. As shown in FIG. 28, the guide wire 1 is fixed to the pusher base portion 20 by the guide wire fixing screw 60. The guide wire 1 and the pusher 4 are then pushed forward together, while maintaining the pricker 1a of the guide wire 1 so that it is protruded slightly from the top end of the drainage tube 3. Then, the pricker 1a is pricked into the duodenum wall 103 while burning it using the high frequency current.

Figure 29:
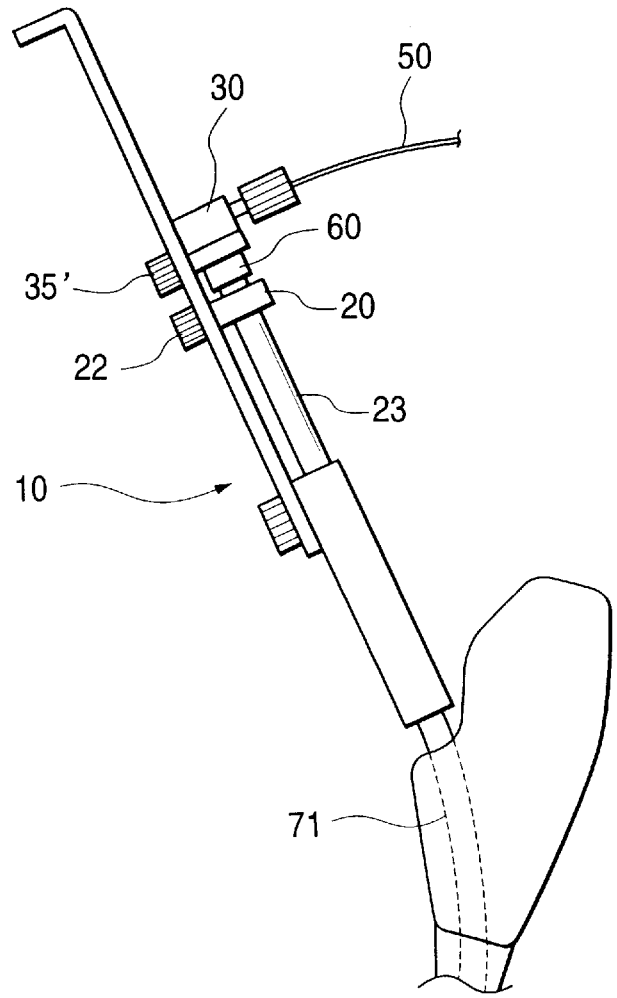
FIG. 29 is a schematic view showing another usage state of the endoscopic drainage tube holder according to the seventh embodiment of the present invention.
Figure 29:
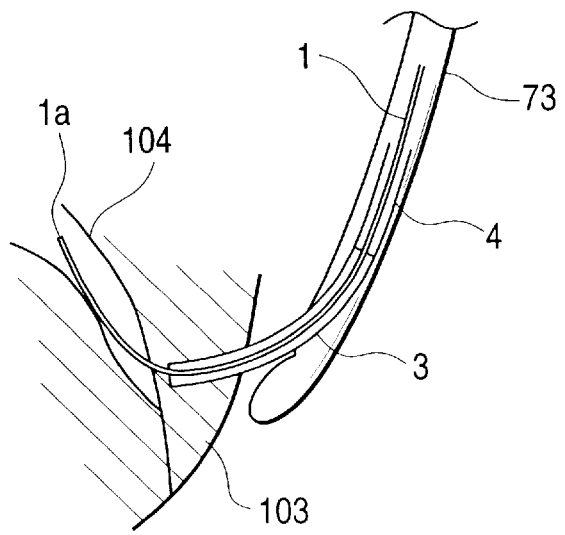

When the pricker 1a of the guide wire 1 is projected slightly into the biliary duct 104, the guide wire fixing screw 60 is loosened. The pusher fixing screw 22 is fixed to the insertion guide 10, and then only the guide wire 1 is pushed out while the high frequency current is not supplied, as shown in FIG. 29. According to the above-described operations, the top end of the guide wire 1 can be inserted more easily into the biliary duct 104.

Figure 30:
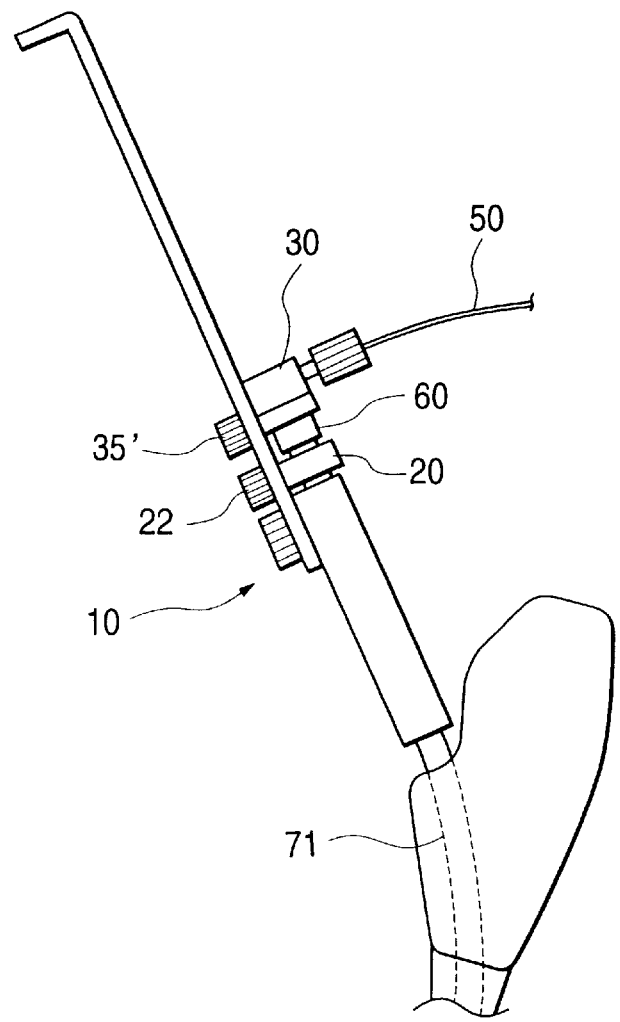
FIG. 30 is a schematic view showing still another usage state of the endoscopic drainage tube holder according to the seventh embodiment of the present invention.
Figure 30:
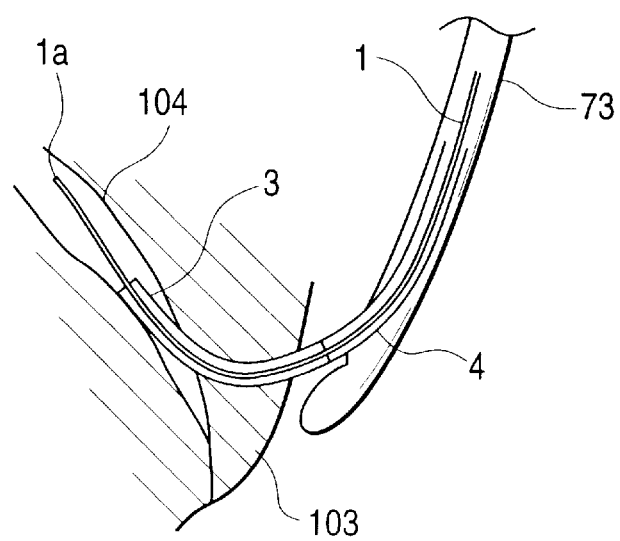

Then, the guide wire 1 is fixed to the pusher base portion 20 by the guide wire fixing screw 60, as shown in FIG. 30. The guide wire 1 and the pusher 4 are pushed forward together, and then the top end portion can be held at a location deep within the biliary duct 104 by using the long drainage tube 3.

Figure 31:
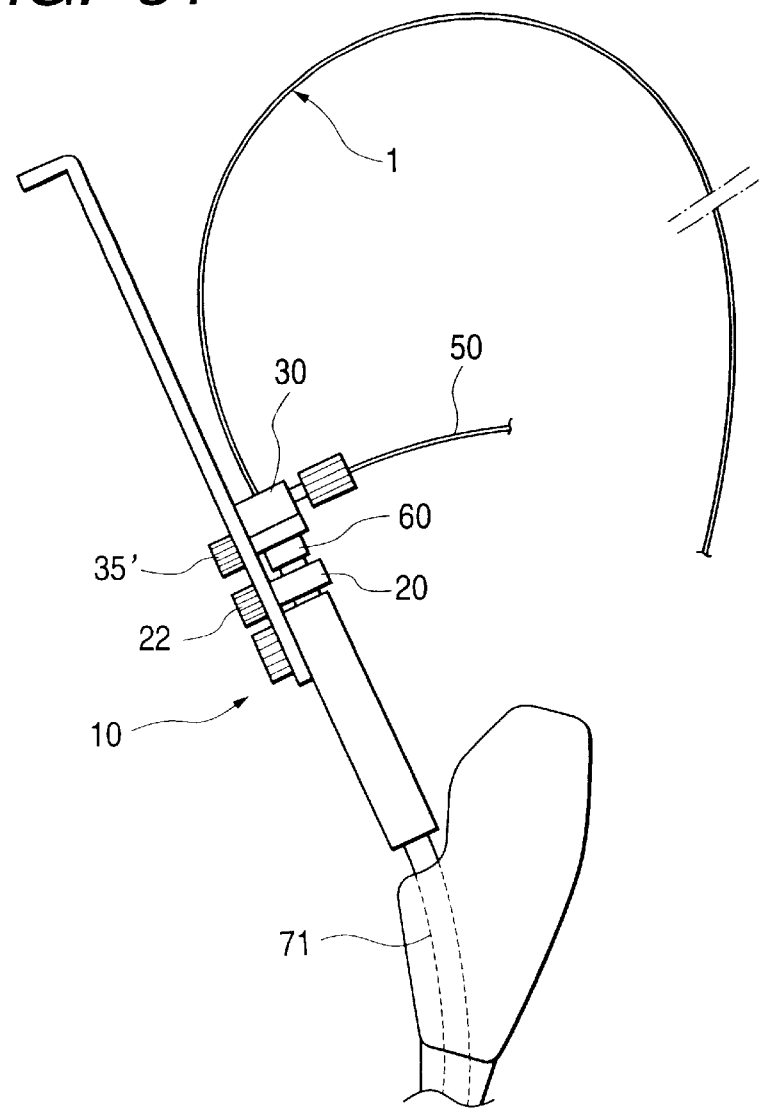
FIG. 31 is a schematic view showing a modification of the endoscopic drainage tube holder according to the seventh embodiment of the present invention.
Figure 31:
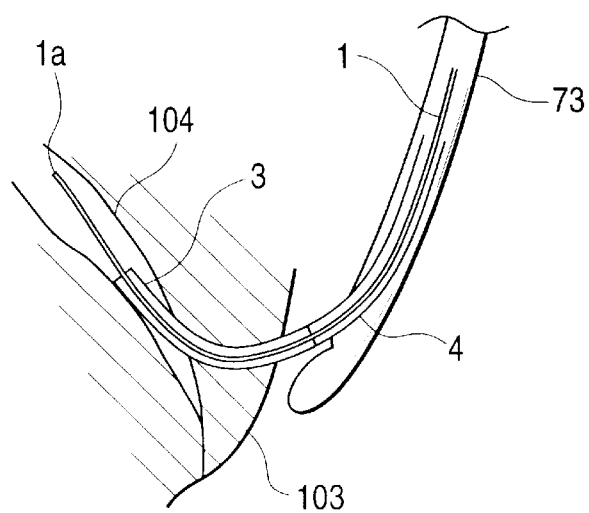

In the above seventh embodiment, as shown in FIG. 31, if the guide wire 1 can be constructed to be inserted/ extracted and fixed into/from the guide wire base portion 30 by setting the guide wire 1 to be longer then twice the length of the pusher 4, only the guide wire 1 can be left and held in the human body. After this, the guide wire 1 can be utilized for various treatments (e.g., to hold the drainage tube in a nose).

In this case, as shown in FIG. 32, the guide wire 1 can be pressed/fixed by the connection terminal 31a, which is screwed into the guide wire base portion 30. A conductive metal portion of the guide wire 1 may be exposed from only the terminal receiving portion 1e to which the connection terminal 31a contacts.

According to the present invention, by fixing the linear guiding member so as not to move when the top end of the linear guiding member is pricked correctly into a target region, the drainage tube can be guided to the holding position quickly by pushing only the pusher from this side. In addition, such operations can be easily conducted by a single endoscope operator. In other words, the endoscope operator does not require assistance.

Moreover, when the linear guiding member is pulled out from the drainage tube after the drainage tube has been set at the correct position, the drainage tube can be held at the correct set position without fail by fixing the drainage tube by the pusher not to move back. In addition, such operations can be conducted easily by a single endoscope operator, without depending on the assistant.

While only certain embodiments of the invention have been specifically described herein, it is apparent that numerous modifications may be made thereto without departing from the spirit and scope of the invention.

What is claimed is:

1. An endoscopic drainage tube holder for insertion into a treating tool insertion channel of an endoscope, said endoscopic drainage tube holder comprising:
a flexible linear guiding member having a pricker at a top end thereof, at a top end side of which a drainage tube is inserted and held;
a pusher, formed of a flexible tube and surrounding said linear guiding member, for pushing said drainage tube in a forward direction;
an insertion guide for guiding at least one of a base end of said pusher and a base end of said linear guiding member, said insertion guide provided on an outside of an inlet of the treating tool insertion channel; and
a fixing unit for fixing at least one of the base end of said pusher and the base end of said linear guiding member to said insertion guide.

2. The endoscopic drainage tube holder according to claim 1, wherein a drainage tube is held around said linear guiding member by a frictional resistance therebetween.

3. The endoscopic drainage tube holder according to claim 2, wherein said fixing unit can fix the base end of said pusher to said insertion guide, independently from the base end of said linear guiding member, when said drainage tube is protruded from an outlet of the treating tool insertion channel.

4. The endoscopic drainage tube holder according to claim 2, wherein said fixing unit can fix the base end of said linear guiding member to said insertion guide, independently from the base end of said pusher when said drainage tube is protruded from an outlet of the treating tool insertion channel.

5. The endoscopic drainage tube holder according to claim 1, wherein the base end of said linear guiding member can be coupled/released to/from the base end of said pusher.

6. The endoscopic drainage tube holder according to claim 1, wherein said pusher and said linear guiding member can be separated from each other, and said pusher and said linear guiding member can be separated from said insertion guide.

7. The endoscopic drainage tube holder according to claim 1, wherein said fixing unit is a fastening screw, and at least one of said linear guiding member and said pusher can be released from said insertion guide by loosening the fastening screw.

8. The endoscopic drainage tube holder according to claim 7, wherein said insertion guide is an L-shaped guide having a long portion and a short portion, and a through hole through which the fastening screw is passed is formed in the short portion to close the through hole.

9. The endoscopic drainage tube holder according to claim 1, wherein said linear guiding member is formed of a conductive guide wire, the pricker at the top end of the guide wire is formed of a high frequency electrode, and a base end side of the guide wire is connected attachably/detachably to a connection terminal to be connected to an electronic power supply for cauterization.

10. The endoscopic drainage tube holder according to claim 9, wherein the flexible tube constituting said pusher is electrically insulative.

11. The endoscopic drainage tube holder according to claim 9, wherein all or apart of the guide wire is coated with an electrically insulating material.

12. The endoscopic drainage tube holder according to claim 1, wherein said linear guiding member is formed of a flexible tube and the pricker is formed like an injection needle.

13. The endoscopic drainage tube holder according to claim 1, wherein said insertion guide has flexibility.

14. The endoscopic drainage tube holder according to claim 3, wherein the base end of said linear guiding member can be fixed/released at any location to/from the base end of said pusher.

15. The endoscopic drainage tube holder according to claim 1, wherein said fixing unit is a manual fixing unit.

16. The endoscopic drainage tube holder according to claim 9, wherein said electronic power supply for cauterization is a high frequency power supply.

* * * * *